(12) United States Patent
Kobayashi

(10) Patent No.: US 9,086,378 B2
(45) Date of Patent: Jul. 21, 2015

(54) METHOD OF ANALYZING IMAGE OF CELL IN LAMINATED STRUCTURE AND METHOD OF EVALUATING LAMINATED STRUCTURE FOR CORNEAL TRANSPLANTATION

(71) Applicant: OLYMPUS CORPORATION, Shibuya-ku, Tokyo (JP)

(72) Inventor: Tamiyo Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 120 days.

(21) Appl. No.: 14/019,363

(22) Filed: Sep. 5, 2013

(65) Prior Publication Data

US 2014/0065639 A1 Mar. 6, 2014

(30) Foreign Application Priority Data

Sep. 6, 2012 (JP) .................................. 2012-195938

(51) Int. Cl.
 *G01N 21/64* (2006.01)
(52) U.S. Cl.
 CPC ........ *G01N 21/6486* (2013.01); *G01N 21/6458* (2013.01)
(58) Field of Classification Search
 USPC ................................................. 382/128–134
 See application file for complete search history.

(56) References Cited

U.S. PATENT DOCUMENTS

| | | | |
|---|---|---|---|
| 6,716,588 B2 * | 4/2004 | Sammak et al. ................ 435/7.2 |
| 8,190,241 B2 * | 5/2012 | Ntziachristos et al. ....... 600/473 |
| 2004/0092825 A1 * | 5/2004 | Madar et al. ................... 600/473 |
| 2006/0014137 A1 * | 1/2006 | Ghosh et al. ........................ 435/4 |
| 2006/0184043 A1 * | 8/2006 | Tromberg et al. ............. 600/476 |
| 2009/0118622 A1 * | 5/2009 | Durkin et al. .................. 600/473 |
| 2010/0078576 A1 * | 4/2010 | Ntziachristos et al. ..... 250/459.1 |
| 2010/0104167 A1 * | 4/2010 | Sakaguchi et al. ............ 382/132 |
| 2010/0285577 A1 * | 11/2010 | Izadyar et al. ................. 435/325 |

(Continued)

FOREIGN PATENT DOCUMENTS

| | | |
|---|---|---|
| JP | 09-281405 A | 10/1997 |
| JP | 2006-343573 A | 12/2006 |

(Continued)

OTHER PUBLICATIONS

Hayashi et al. "Validation System of Tissue-Engineered Epithelial Cell Sheets for Corneal Regenerative Medicine", Tissue Engineering: Part C, vol. 16, No. 4, 2009, p. 553-560.

*Primary Examiner* — Alex Liew
(74) *Attorney, Agent, or Firm* — Holtz, Holtz, Goodman & Chick PC

(57) ABSTRACT

A method of analyzing an image of a cell in a laminated structure may include the steps of: (a) fluorescently labeling a cell nucleus in the laminated structure having at least one cell layer and one or more other types of biomolecules; (b) acquiring a plurality of planar tomographic fluorescent labeled images in different height directions from the laminated structure for each type of fluorescently labeled biomolecules after the step (a); (c) superimposing a planar tomographic fluorescent labeled image group acquired in the step (b) to construct a three-dimensional tomographic image; (d) dividing the three-dimensional tomographic image constructed in the step (c) into one or two or more cell regions; (e) producing one planar stacked image for each divided cell region after the step (d); and (f) performing image analysis on each planar stacked image produced in the step (e) to analyze cells in the laminated structure.

21 Claims, 16 Drawing Sheets

(56) References Cited

U.S. PATENT DOCUMENTS

2011/0240884 A1* 10/2011 Yamamoto .................. 250/458.1
2011/0243414 A1* 10/2011 Yamamoto et al. ........... 382/131
2013/0017570 A1* 1/2013 Ohashi ............................ 435/34
2014/0065639 A1* 3/2014 Kobayashi .................... 435/7.1

FOREIGN PATENT DOCUMENTS

| | | |
|---|---|---|
| JP | 2009-175334 A | 8/2009 |
| JP | 2011-075278 | 4/2011 |

* cited by examiner

Lower

Upper

Merged

Lower

Upper

Merged

METHOD OF ANALYZING IMAGE OF CELL IN LAMINATED STRUCTURE AND METHOD OF EVALUATING LAMINATED STRUCTURE FOR CORNEAL TRANSPLANTATION

BACKGROUND OF THE INVENTION

1. Field of the Invention

The present invention relates to a method of analyzing a laminated structure, which includes cell populations forming a layered structure, in a state of a three-dimensional structure by imaging (image) and a method of evaluating a laminated structure for use in corneal transplantation using the image analysis method.

Priority is claimed on Japanese Patent Application No. 2012-195938, filed Sep. 6, 2012, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In recent years, for the purpose of regenerating damaged biological tissues or organs, regenerative medicine using stem cells has attracted attention. A treatment method in which a structure obtained by culturing stem cells from a patient and forming a three-dimensional structure similar to a tissue is transplanted is excellent in that, unlike organ transplantation, there are no rejection and donor insufficiency. Actually, treatment in which a laminated structure formed by culturing epithelial stem cells, such as corneal epithelial stem cells and oral mucosal stem cells from a patient, is transplanted to a cornea so as to regenerate the cornea is put into practical use.

In general, stem cells are transplanted as a laminated structure in which a layer having differentiated cells is formed above a layer of stem cells, or a laminated structure in which a plurality of single-layered structures having only a layer of stem cells formed are superimposed. Each cell in the laminated structure transplanted to the biological tissue is proliferated and differentiated after engraftment, and as a result, the biological tissue is regenerated. Whether or not a damaged biological tissue is sufficiently generated by transplantation of a laminated structure for transplantation depends on the quality of the laminated structure for transplantation. For this reason, the evaluation of the quality of the laminated structure for transplantation is important.

In regard to the evaluation of the quality of the laminated structure for corneal transplantation, for example, in "Tissue Engineering: Part C, Hayashi and seven others, 2009, Vol. 16, No. 4, pp. 553 to 560" (hereinafter, referred to as Non-Patent Literature 1), first, the laminated structure for corneal transplantation is divided into halves. Then, one half is divided into individual cells, and the total number of cells, the number of living cells, and the number of cytokeratin-positive cells (that is, the number of epithelial cells) are quantitatively measured by flow cytometry. Frozen sections (having a thickness is about 10 um) are created from the other half, each section is subjected to HE staining or immunostaining for p63, AE5, ZO-1, and MUC16, the states of the cells are examined, and the results are synthesized to evaluate the quality.

In the evaluation method described in Non-Patent Literature 1, since the frozen sections are analyzed, only a considerably small part of the laminated structure for corneal transplantation can be evaluated, and multi-dimensional analysis is impossible. That is, it is not possible to analyze the positional relationship of the cells in the laminated structure for corneal transplantation. It also takes a lot of time and effort to divide the laminated structure for corneal transplantation. In addition, a worker should have proficiency in producing frozen sections, and in many cases, there is a difference between samples.

The invention provides a method of more simply analyzing images of a laminated structure, which includes cell populations forming a layered structure, while maintaining information regarding the positional relationship between cells in the laminated structure, and a method of evaluating a laminated structure for corneal transplantation using the image analysis method.

SUMMARY OF THE INVENTION

A method of analyzing an image of a cell in a laminated structure may include the steps of:

(a) fluorescently labeling a cell nucleus in the laminated structure having at least one cell layer and one or more other types of biomolecules;

(b) acquiring a plurality of planar tomographic fluorescent labeled images in different height directions from the laminated structure for each type of fluorescently labeled biomolecules after the step (a);

(c) superimposing a planar tomographic fluorescent labeled image group acquired in the step (b) to construct a three-dimensional tomographic image;

(d) dividing the three-dimensional tomographic image constructed in the step (c) into one or two or more cell regions;

(e) producing one planar stacked image for each divided cell region after the step (d); and (f) performing image analysis on each planar stacked image produced in the step (e) to analyze cells in the laminated structure, wherein the cell regions divided in the step (d) may be regions which include one or two or more cell layers in the three-dimensional tomographic image and are parallel to the bottom of the three-dimensional tomographic image.

In the step (d), a cell region of one cell layer including a specific type of cells from among the determined cell regions may be determined by the steps of:

(i) specifying, as a cell-free cross section, a cross section, in which there are no cell nuclei of the specific type of cells and which has the smallest height from the bottom of the laminated structure, from among cross sections parallel to the bottom of the three-dimensional tomographic image;

(ii) specifying, as a cell bottom reference cross section, a cross section, which is located above the cell-free cross section, has the total luminance value of cells to be analyzed per image of the cell nucleus labeled image 10 to 50% greater than the cell-free cross section, and is closest to the cell-free cross section, from among the cross sections parallel to the bottom of the three-dimensional tomographic image; and (iii) determining, as the cell region of the cell layer including the specific type of cells, a region from a cross section located 5 to 10 µm below the cell bottom reference cross section in the height direction of the laminated structure to a cross section located 15 to 25 µm above the cell bottom reference cross section in the height direction of the laminated structure.

The specific type of cells may be stem cells.

The laminated structure may have a first cell layer including a first type of cells, and a second cell layer including a second type of cells different from the first type above the first cell layer.

In the step (a), in addition to the cell nucleus, one or more types of biomolecules selected from a group including biomolecules more expressed in the first type of cells than the second type of cells and biomolecules more expressed in the second type of cells than the first type of cells may be fluorescently labeled.

The first type of cells may be stem cells, and the second type of cells may be cells which are differentiated from the stem cells.

In the step (d), a cell region of the first cell layer and a cell region of the second cell layer may be divided.

The laminated structure may be formed by culturing corneal epithelial stem cells or oral mucosal stem cells.

During the image analysis in the step (f), one or more selected from a group including an average luminance value per pixel of each planar stacked image, the sum of luminance values of all pixels, the total area of pixels having a luminance value per pixel equal to or greater than a threshold value, and the shape of a region of pixels having a luminance value per pixel equal to or greater than the threshold value may be analyzed.

A method of evaluating a laminated structure for corneal transplantation which is formed by culturing epithelial stem cells and used for corneal transplantation may include the steps of:

(a') fluorescently labeling a cell nucleus in the laminated structure and one or more types of biomolecules selected from a group including biomolecules specific to epithelial stem cells, biomolecules specific to epithelial cells after differentiation or a surrounding tissue, and biomolecules in both the epithelial stem cells and the epithelial cell after differentiation;

(b') acquiring a plurality of planar tomographic fluorescent labeled images in different height directions from the laminated structure for each type of fluorescently labeled biomolecules after the step (a');

(c') superimposing a planar tomographic fluorescent labeled image group acquired in the step (b') to construct a three-dimensional tomographic image;

(d') dividing the three-dimensional tomographic image constructed in the step (c') into a lower cell region of a cell layer including epithelial stem cells and an upper cell region above and adjacent to the lower cell region;

(e') producing one planar stacked image for each divided region after the step (d'); and (f') performing image analysis on each planar stacked image produced in the step (e') and evaluating the laminated structure on the basis of the obtained analysis result, wherein the cell regions divided in the step (d') may be regions which include one or two or more cell layers in the three-dimensional tomographic image and are parallel to the bottom of the three-dimensional tomographic image.

In the step (d'), the lower cell region may be determined by the steps of:

(i') specifying, as a cell-free cross section, a cross section, in which there are no cell nuclei and which has the smallest height from the bottom of the laminated structure, from among cross sections parallel to the bottom of the three-dimensional tomographic image;

(ii') specifying, as a stem cell bottom reference cross section, a cross section which is located above the cell-free cross section, has a total luminance value per image of the cell nucleus labeled image 10 to 50% greater than the cell-free cross section, and is closest to the cell-free cross section, from among the cross sections parallel to the bottom of the three-dimensional tomographic image; and (iii') determining, as the lower cell region, a region from a cross section 5 to 10 µm below the stem cell bottom reference cross section in the height direction of the laminated structure to a cross section 15 to 25 µm above the stem cell bottom reference cross section in the height direction of the laminated structure.

In the step (d'), the upper cell region and the lower cell region may be determined by the steps of:

(i"-1) specifying, as a lower cell-free cross section, a cross section, in which there are no cell nuclei and which has the smallest height from the bottom of the laminated structure, from among cross sections parallel to the bottom of the three-dimensional tomographic image;

(i"-2) specifying, as an upper cell-free cross section, a cross section, in which there are no cell nuclei and which has the greatest height from the bottom of the laminated structure, from among the cross sections parallel to the bottom of the three-dimensional tomographic image; and (iii") defining a cross section at the same distance from both the lower cell-free cross section and the upper cell-free cross section as an interface, determining a region from the lower cell-free cross section to the interface as the lower cell region, and determining a region from the interface to the upper cell-free cross section as the upper cell region.

In the step (a'), the cell nucleus and one or more types of biomolecules selected from a group including cytokeratin, mucin, and biomolecules constituting the tight junction of epithelial cells, and p63 may be fluorescently labeled.

In the step (a'), the cell nucleus and one or more types of biomolecules selected from a group including AE5, MUC16, ZO-1, panCK, and p63 may be fluorescently labeled.

In the step (a'), at least the cell nucleus and AE5 may be fluorescently labeled.

In the step (f'), when an average luminance value per pixel in a fluorescent labeled image of AE5 of a planar stacked image produced from the upper cell region, the sum of the luminance values of all pixels, and the total area of pixels having a luminance value per pixel equal to or greater than a threshold value are greater than a fluorescent labeled image of AE5 of a planar stacked image produced from the lower cell region, it may be evaluated that the laminated structure is appropriate for corneal transplantation.

In the step (a'), at least the cell nucleus and MUC16 may be fluorescently labeled.

In the step (f'), when an average luminance value per pixel in a fluorescent labeled image of MUC16 of a planar stacked image produced from the upper cell region, the sum of the luminance values of all pixels, and the total area of pixels having a luminance value per pixel equal to or greater than a threshold value are greater than a fluorescent labeled image of MUC16 of a planar stacked image produced from the lower cell region, it may be evaluated that the laminated structure is appropriate for corneal transplantation.

In the step (a'), at least the cell nucleus and ZO-1 may be fluorescently labeled.

In the step (f'), when an average luminance value per pixel in a fluorescent labeled image of ZO-1 of a planar stacked image produced from the upper cell region, the sum of the luminance values of all pixels, and the total area of pixels having a luminance value per pixel equal to or greater than a threshold value are greater than a fluorescent labeled image of ZO-1 of a planar stacked image produced from the lower cell region, and a region of pixels having a luminance value per pixel equal to or greater than a threshold value in the fluorescent labeled image of ZO-1 of the planar stacked image produced from the upper cell region has a shape of a network structure, it may be evaluated that the laminated structure is appropriate for corneal transplantation.

In the step (a'), at least the cell nucleus and p63 may be fluorescently labeled.

In the step (f'), for each planar stacked image produced in the step (e'), a cell nucleus region may be determined on the basis of a labeled image of the cell nucleus.

When an average luminance value per pixel in each cell nucleus region in a labeled image of p63 of a planar stacked image produced from the upper cell region is greater than a fluorescent labeled image of p63 of a planar stacked image produced from the lower cell region, it may be evaluated that the laminated structure is appropriate for corneal transplantation.

In the step (f'), for each planar stacked image produced in the step (e'), a cell nucleus region may be determined on the basis of a labeled image of the cell nucleus.

When the ratio of the cell nucleus region having an area equal to or greater than a threshold value to all cell nucleus regions in a planar stacked image produced from the upper cell region is greater than a planar stacked image produced from the lower cell region, it may be evaluated that the laminated structure is appropriate for corneal transplantation.

In the step (f'), for each planar stacked image produced in the step (e'), a cell nucleus region may be determined on the basis of a labeled image of the cell nucleus.

When the average value of the areas of the cell nucleus regions in a planar stacked image produced from the upper cell region is three times greater than the average value of the areas of the cell nucleus regions in a planar stacked image produced from the lower cell region, it may be evaluated that the laminated structure is appropriate for corneal transplantation.

In the step (a'), panCK may be further fluorescently labeled.

In the step (f'), for each planar stacked image produced in the step (e'), a cell nucleus region may be determined on the basis of a labeled image of the cell nucleus.

A region which is a doughnut-shaped region with the outer circumferential portion of each cell nucleus region as an inner circumference and in which the width of the doughnut shape has a regular interval may be determined as a cytoplasmic region.

When an average luminance value per pixel in each cytoplasmic region of a labeled image of panCK of a planar stacked image produced from the upper cell region is the same as a fluorescent labeled image of panCK of a planar stacked image produced from the lower cell region, it may be evaluated that the laminated structure is appropriate for corneal transplantation.

With the method of analyzing an image of a cell in the laminated structure according to the invention, it is possible to efficiently analyze a state where cells are laminated, without dividing the cells.

For this reason, with the method of evaluating a laminated structure for corneal transplantation according to the invention using the image analysis method, it is possible to efficiently evaluate the laminated structure for corneal transplantation including the positional relationship between epithelial stem cells and differentiated cells in the structure.

With the method of analyzing an image of a cell in the laminated structure according to the invention, since simultaneous multi-staining can be performed, and a wide region (wide range) of the laminated structure can be observed and analyzed at one time, it is also possible to reduce the analysis time.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE INVENTION

Figure 1:
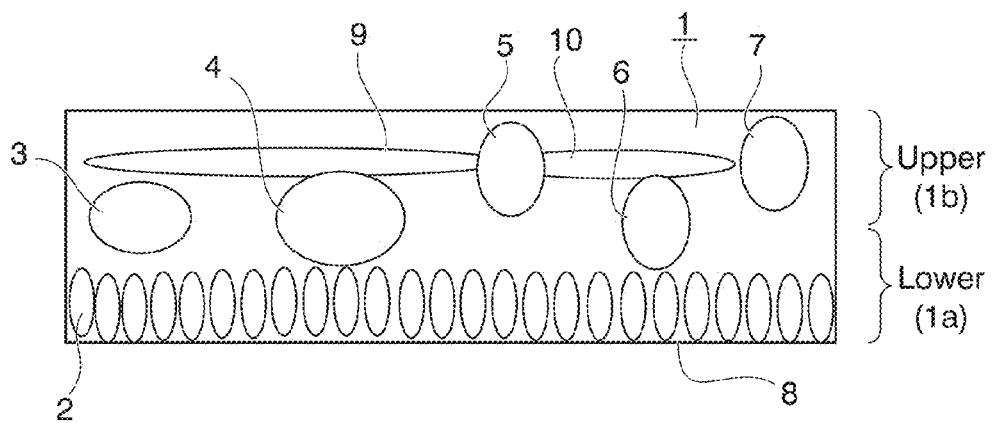
FIG. 1 is a diagram schematically showing an example in which a laminated structure having a stem cell layer below and a cell layer of differentiated cells above the stem cell layer is divided into two cell regions of a lower cell region having the stem cell layer and an upper cell region having the cell layer of differentiated cells.

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated for explanatory purpose.

(Method of Analyzing Image of Cell in Laminated Structure)

A method of analyzing an image of a cell in a laminated structure of the invention (hereinafter, referred to as an image analysis method of the invention.) includes the steps of:

(a) fluorescently labeling a cell nucleus in the laminated structure having at least one cell layer and one or more other types of biomolecules;

(b) acquiring a plurality of planar tomographic fluorescent labeled images in different height directions from the laminated structure for each type of fluorescently labeled biomolecules after the step (a);

(c) superimposing a planar tomographic fluorescent labeled image group acquired in the step (b) to construct a three-dimensional tomographic image;

(d) dividing the three-dimensional tomographic image constructed in the step (c) into one or two or more cell regions;

(e) superimposing all planar tomographic fluorescent labeled images included in each divided cell region to produce one planar stacked image after the step (d); and (f) performing image analysis on each planar stacked image produced in the step (e) to analyze cells in the laminated structure, in which cell regions divided in the step (d) are regions which include one or two or more cell layers in a three-dimensional tomographic image and are parallel to the bottom of the three-dimensional tomographic image.

That is, in the image analysis method of the invention, while the laminated structure which includes cell populations forming a layered structure is maintained to be a three-dimensional structure, after the cell nucleus and various biomolecules are fluorescently labeled, a plurality of planar tomographic fluorescent labeled image in different height directions of the laminated structure are acquired, and the obtained planar tomographic fluorescent labeled image group is superimposed to construct a three-dimensional tomographic image. A layered cell region including cell population to be analyzed is divided from the obtained three-dimensional tomographic image, and all planar tomographic fluorescent labeled images in the cell region are superimposed to produce one planar stacked image. Image analysis is performed on the obtained planar stacked image.

Detailed image analysis on a three-dimensional image causes an enormous amount of data to be handled and requires an excessively long time. In contrast, in the invention, since a layered region including cell populations to be analyzed in a three-dimensional tomographic image is lowered in dimension and defined as a planar stacked image, and image analysis is performed on the planar stacked image, analysis on each cell population is performed on a planar image, thereby efficiently performing detailed image analysis taking into consideration information regarding the positional relationship of cells in a laminated structure.

In the invention and the specification, a laminated structure refers to a structure which has two or more layers and in which at least one layer is a cell layer. A layer is a region which is substantially parallel to the bottom of the structure and has a certain thickness in the height direction, and a cell layer is a layer of populations of homogeneous cells or cells having similar properties and substantially a cell population formed in a single layer. A laminated structure to be analyzed by the image analysis method of the invention may be a structure in which two or more cell layers are laminated. A structure in which one or more cell layers and one or more layers including no cells are laminated may be used. When a laminated structure has two or more cell layers, all cell layers may be cell layers including homogeneous cells, or two or more cell layers including different types of cells may be provided. As a layer other than a cell layer in a laminated structure, for example, an extracellular matrix, a basement membrane layer to which cells are bonded and cultured, or the like may be used. As a membrane constituting the basement membrane layer, for example, a polymer membrane, a membrane in which biomolecules, such as protein or carbohydrate, are coated on the surface, an amnion, or the like may be used. A membrane artificially manufactured may be used, and a tissue slice from a living body while maintaining a layered structure may be used.

It is preferable that a laminated structure to be analyzed by the image analysis method of the invention is a laminated structure which has two or more cell layers. A laminated structure which has only two or more cell layers may be used, and a laminated structure which includes a basement membrane layer or the like in addition to two or more cell layers may be used. Of these, a laminated structure in which at least one cell layer is a cell layer (stem cell layer) including stem cells as a main component is preferably used. As the laminated structure, a laminated structure which has two or more stem cell layers may be used, or a laminated structure which has a stem cell layer and a cell layer including other cells as a main component may be used. As a laminated structure which has two or more stem cell layers, for example, a structure in which stem cell layers are laminated directly, a structure in which a basement membrane layer is located between stem cell layers, or the like may be used. As a laminated structure which has a stem cell layer and a cell layer including other cells, a structure in which a stem cell layer is located below and a layer including cells differentiated from the stem cells is located above the stem cell layer adjacent to the stem cell layer or through a basement membrane layer or the like, or the like may be used.

A laminated structure to be analyzed by the image analysis method of the invention is preferably a laminated structure which has one or more stem cell layers and is used for transplantation to a living body, and more preferably, a laminated structure for corneal transplantation which is transplanted to a cornea. As a laminated structure for corneal transplantation, for example, a structure in which a stem cell layer including epithelial stem cells is located below and a cell layer including cells differentiated from epithelial stem cells is located adjacent to the upper surface of the stem cell layer, a structure in which stem cell layers including epithelial stem cells is laminated, or the like may be used. As epithelial stem cells, corneal epithelial stem cells, oral mucosal stem cells, or the like may be used.

A laminated structure to be analyzed by the image analysis method of the invention may be produced or extracted by any known method in the art. For example, as described in Non-Patent Literature 1, a cell suspension including stem cells is placed on the bottom of a cultivation container and cultured, thereby forming a laminated structure having cells staked in multiple layers. A stem cell layer of stem cells cultured in a single layer on the surface of a basement membrane layer is superimposed along with a basement membrane layer, or only stem cell layers are superimposed, thereby forming a laminated structure.

Hereinafter, each step will be described.

First, in the step (a), a cell nucleus and one or more other types of biomolecules in a laminated structure having at least one cell layer are fluorescently labeled. As the biomolecules, protein, nucleic acid, saccharides, lipid, or the like may be used. The biomolecules to be fluorescently labeled may be of one type or two or more types. Multi-fluorescent staining is performed, thereby reducing the analysis time of the laminated structure.

When a laminated structure has two or more cell layers having different types of cells as a main component, it is preferable that biomolecules for identifying cells constituting each cell layer are fluorescently labeled. For example, when a laminated structure has a first cell layer including a first type of cells and a second cell layer including a second type of cells different from the first type above the first cell layer, it is preferable that at least one type of biomolecules selected from a group including biomolecules more expressed in the first type of cells than the second type of cells and biomolecules more expressed in the second type of cells than the first type of cells is fluorescently labeled.

The cell nucleus can be fluorescently labeled by fluorescently labeling nucleic acid in the cell nucleus. A fluorescent nucleic acid stain which is used for fluorescent staining of nucleic acid may be appropriated selected and used from known fluorescent nucleic acid stains, such as a fluorescent DNA intercalator. Examples of a fluorescent DNA intercalator include DAPI (4',6-diamino-2-phenylindole), PI (propidium iodide), Hoechst33258, Hoechst33342, 7-AAD (7 Amino actinomycin D), DRAQ5 (Registered Trademark) (manufactured by Biostatus), Sytox (Registered Trademark) (manufactured by Invitrogen), YOYO (Registered Trademark) (manufactured by Invitrogen), and the like.

Fluorescent labeling of biomolecules is not particularly limited insofar as fluorescent labeling can be performed so as to visually distinguish between biomolecules and a cell nucleus on an image captured by detecting fluorescence emitted through irradiation of excitation light having an appropriate wavelength, and any known method in the art may be used.

For example, an antibody, a ligand, or the like to be specifically bound to biomolecules is used, and immunofluorescent staining using a primary antibody or a secondary antibody with a fluorescent material bound thereto is performed. Immunofluorescent staining is generally used in the art and can be performed in the usual manner.

For example, when one type or a plurality of types of biomolecules are immunofluorescently stained, and a cell nucleus is stained using a fluorescent nucleic acid stain, such as DAPI, it is preferable that the fluorescent characteristic of a fluorescent material staining each biomolecule and the fluorescent characteristic of the fluorescent nucleic acid stain are different from each other. The difference in fluorescent characteristic means that the wavelength of fluorescence emitted through irradiation of excitation light differs so as to be distinctively detected, like FITC and rhodamine.

Specific binding means that an antibody or the like may be specifically bound so as to be usually used for detection or purification of a material to which the antibody is bound, and an antibody may cross other materials. An antibody against biomolecules for fluorescent labeling of the biomolecules may be a monoclonal antibody, or may be a polyclonal antibody. A commercially available antibody may also be used, or an antibody which immunizes an experimental animal with the biomolecules or the biomolecule portion as an antigen and is produced in the usual manner may be used.

The laminated structure which is served in the step (a) may be in a state where cells in the laminated structure are alive, and may be a laminated structure which is fixed to a cell observation container or a laminated structure which is subjected to cell membrane permeation processing using a surfactant or the like after fixing.

It should suffice that the laminated structure is bonded to the cell observation container, and fixing processing is not necessarily performed. A method of fixing a laminated structure to the cell observation container is not particularly limited, and may be performed in the usual manner. For example, natural drying may be performed, or a cell fixing cross-linking agent, such as formaldehyde, paraformaldehyde, or methanol may be used to fix the laminated structure to the cell observation container.

Although the cell observation container is not particularly limited insofar as a container is generally used for cell staining, a slide glass or a multi-well plate is preferably used. An imaging cytometer or the like is used using a glass slide or a multi-well plate, making it possible to process multiple samples rapidly and simply.

Next, in the step (b), a plurality of planar tomographic fluorescent labeled images in different height directions are acquired from the laminated structure for each type of the fluorescent labeled biomolecules. A plurality of planar tomographic fluorescent labeled images in different height directions can be captured and acquired in the usual manner.

For example, while shifting a confocal region little by little in the height direction (Z-axis direction) of the laminated structure using a confocal laser microscope or the like (relatively moving an objective lens and a laminated structure in a direction perpendicular to the optical axis), a planar tomographic fluorescent labeled image of a cross section parallel to the bottom of the laminated structure is sequentially captured, thereby acquiring a plurality of planar tomographic fluorescent labeled images in different height directions. With a confocal microscope, it is advantageous in that it is possible to automatically perform wide-range observation and analysis on a thick laminated structure in the depth direction and in plan view without creating sections.

In the invention, for each shot (each microscopic field), fluorescent labeled images of all biomolecules and the cell nucleus fluorescently labeled in the step (a) are acquired. Specifically, for each shot, excitation light having a wavelength according to the fluorescent characteristic of each fluorescent material is sequentially irradiated, and emitted fluorescence is detected to capture an image.

These images can be captured and acquired using an imaging apparatus, such as a CCD camera, which is usually used to capture cells. For example, during imaging using the CCD camera, usually, one or a plurality of images are captured for individual XY positions. There are many cases where an imaging point is specified by defining the focal position of a lens as, for example, Z and setting an XY plane in a plane perpendicular to Z. An image of each channel captured by the CCD camera is a monochrome image, and for example, each value of 0 to 4096 is allocated to each respective XY position (each pixel of the image) for each brightness level to record luminance of each pixel.

In the step (b), when acquiring planar tomographic fluorescent labeled images at a specific height (a specific position on the Z axis) of the laminated structure, a plurality of planar tomographic fluorescent labeled images at different XY positions may be acquired. A planar tomographic fluorescent labeled image group at the same height is pasted in a tiled shape, and thus a very wide range of the laminated structure can be subjected to image analysis.

For example, the XY plane (the plane parallel to the bottom) of the laminated structure is divided into a plurality of small segments, and the planar tomographic fluorescent labeled images of the respective small segments are acquired and pasted to form one planar tomographic fluorescent labeled image. It is preferable that the small segments are set such that end image regions of adjacent small segments in the X-axis direction or the Y-axis direction overlap each other.

Next, in the step (c), the planar tomographic fluorescent labeled image group acquired in the step (b) is superimposed, thereby constructing a three-dimensional tomographic image. The fluorescently labeled images individually acquired in the step (b) are superimposed. Accordingly, the constructed three-dimensional tomographic image can be separated into a labeled image for each type of substance fluorescently labeled in the step (a), for example, the fluorescent labeled image (cell nucleus labeled image) of the cell nucleus and the fluorescent labeled images of the respective biomolecules.

The construction of the three-dimensional tomographic image can be performed by, for example, a known image construction method in the art of computer tomography (CT). As a method in which a plurality of planar tomographic fluorescent labeled images acquired while relatively moving the objective lens and the laminated structure in a direction with respect to the optical axis are superimposed to produce a three-dimensional tomographic image, specifically, a method described in Japanese Unexamined Patent Application, First Publication No. 2006-343573, No. H09-281405, No. 2009-175334, or the like may be used.

In the step (d), one or two or more cell regions are divided from the three-dimensional tomographic image constructed in the step (c). The cell regions are regions which include one or two or more cell layers and are parallel to the bottom.

In this step, only one cell region or two or more cell regions may be divided from the three-dimensional tomographic image. For example, when the laminated structure includes different types of cells between the lower region and the upper region, two cell regions of a cell region having one or two or more cell layers of cells in the lower region and a cell region having one or two or more cell layers of cells in the upper region can be divided from the three-dimensional tomographic image.

Similarly, when the laminated structure includes different types of cells among the lower region, the upper region, and a region between the lower region and the upper region, three cell regions of a cell region having one or two or more cell layers having cells in the lower region, a cell region having one or two or more cell layers of cells in the region between the lower region and the upper region, and a cell region having one or two or more cell layers of cells in the upper region can be divided from the three-dimensional tomographic image.

When the laminated structure is a structure in which stem cell layers and basement membrane layers are alternately laminated, each stem cell layer sandwiched between the basement membrane layers can be divided as a cell region. When the laminated structure is a structure in which a stem cell layer is located below and a cell layer of differentiated cells is located above the stem cell layer, two cell regions of a cell region having the stem cell layer and a cell region having the cell layer of the differentiated cells can be divided from the three-dimensional tomographic image. FIG. 1 is a schematic view when the laminated structure is divided into two cell regions.

In FIG. 1, a layer of stem cells 2 is formed on a lower side of a laminated structure 1 provided in a cell observation container 8, and differentiated cells 3 to 7, 9 and 10 are located on an upper side. The laminated structure 1 can be divided into a lower cell region 1a having a cell layer of stem cell 2 and an upper cell region 1b having a cell layer of differentiated cells. In the upper cell region 1b, the differentiated cells may be separated into two or more cell populations according to the degree of differentiation, and cell regions may be divided for the respective cell populations.

The interface of the cell regions may be determined visually from the three-dimensional tomographic image, or may be determined according to a given reference defined in advance. When a cell region to be analyzed is determined according to a given reference, it is possible to reduce a difference by subjective determination of an analyzer.

For example, when a cell region is a region which includes only one cell layer with a cell population forming a single layer, and when the thickness of the cell region (the width in the height direction of the laminated structure) is excessively large, many regions other than an intended cell layer are included in the cell region, and noise or the like may increase in a formed planar stacked image.

To the contrary, if the thickness of the cell region is near an average thickness (hereinafter, referred to as "standard cell thickness") of cells forming an intended cell layer, a part of a cell population constituting a cell layer may not be included in a cell region. This is because it is not always true that all cells forming a layered structure are located exactly at the same height in the laminated structure.

Accordingly, from among the cell regions to be determined, a cell region having one cell layer of a specific type of cells (cells to be analyzed) can be determined in the following manner.

First, from among cross sections parallel to the bottom of the three-dimensional tomographic image, a cross section in which there are no cell nuclei of cells to be analyzed and which has the smallest height from the bottom of the laminated structure is specified as a cell-free cross section. Usually, since there are no cells at the bottom of the laminated structure, the bottom or a neighboring cross section can be specified as a cell-free cross section. From among the cross sections parallel to the bottom of the three-dimensional tomographic image, a cross section which is located above the cell-free cross section, has a total luminance value of cells to be analyzed per image of a cell nucleus labeled image 10 to 50%, preferably, 15 to 40% greater than the cell-free cross section, and is closest to the cell-free cross section is specified as a cell bottom reference cross section.

A cross section 5 to 10 μm below the cell bottom reference cross section in the height direction of the laminated structure is a lower interface of the cell region, and a cross section 15 to 25 μm above the lower interface in the height direction of the laminated structure is an upper interface of the cell region. That is, a region from the cross section 5 to 10 μm below the cell bottom reference cross section in the height direction of the laminated structure to the cross section 15 to 25 μm above in the height direction is determined as a cell region having a cell layer of cells to be analyzed.

It is considered that the cross section 15 to 25 μm above the lower interface is defined as the upper interface, and thus in a region from the lower interface to the upper interface, at least 80% or more of all cells to be analyzed in a cell layer is located. The cell thickness of the cells to be analyzed is taken into consideration, and the cross section 5 to 10 μm below the cell bottom reference cross section is defined as the lower interface of the cell region. The upper interface may be a cross section, in which there are no cell nuclei and which is closest to the cell bottom reference cross section, from among cross sections parallel to the bottom above the cell bottom reference cross section. The lower interface may be a cross section, in which there are no cell nuclei and which is closest to the cell bottom reference cross section, from among cross sections parallel to the bottom below the cell bottom reference cross section.

In many cells, one cell nucleus is included in one cell. Accordingly, the number of cells to be analyzed in a cross section parallel to the bottom of the three-dimensional tomographic image is obtained by measuring the number of cell nuclei in the cross section. The cell nuclei in each cross section of the three-dimensional tomographic image is obtained by determining a cell nucleus region from the cell nucleus labeled image of each cross section and counting the number of cell nucleus regions. The determination of a cell nucleus region from a cell nucleus labeled image can be done by, for example, a method described in Japanese Unexamined Patent Application, First Publication No. 2011-75278, or the like.

Specifically, the cell nucleus region can be determined by the following method. First, a cell nucleus threshold value and a cell nucleus area threshold value for recognizing the cell nucleus in the cell nucleus labeled image are set in advance, and a group of regions where each pixel has a value (hereinafter, referred to as "luminance value") of luminance equal to or greater than the cell nucleus threshold value is recognized as a main object from the cell nucleus labeled image.

The boundary of the object is separated from the gradient of the luminance value of each pixel in the object, and a region having an area equal to or greater than the cell nucleus area threshold value in the closed region is extracted and determined as a cell nucleus region.

The term "luminance" used herein is a value which represents shading in a gray-scale image and a value which represents brightness of each pixel in an image. The term "area" used herein may mean the number of pixels in a region as well as a numerical value of an accurate area of a region.

The cell nucleus threshold value and the cell nucleus area threshold value are appropriately set taking into consideration the type of cells to be analyzed, the type of fluorescent nucleic acid stain using labeling of nucleic acid. For example, after cells of the same type of cells to be analyzed are stained using a fluorescent nucleic acid stain in advance to acquire a cell nucleus labeled image, the luminance value or area value of the cell nucleus region is measured from the cell nucleus labeled image, and the cell nucleus threshold value and the cell nucleus area threshold value can be set by the measured value.

Figure 2:
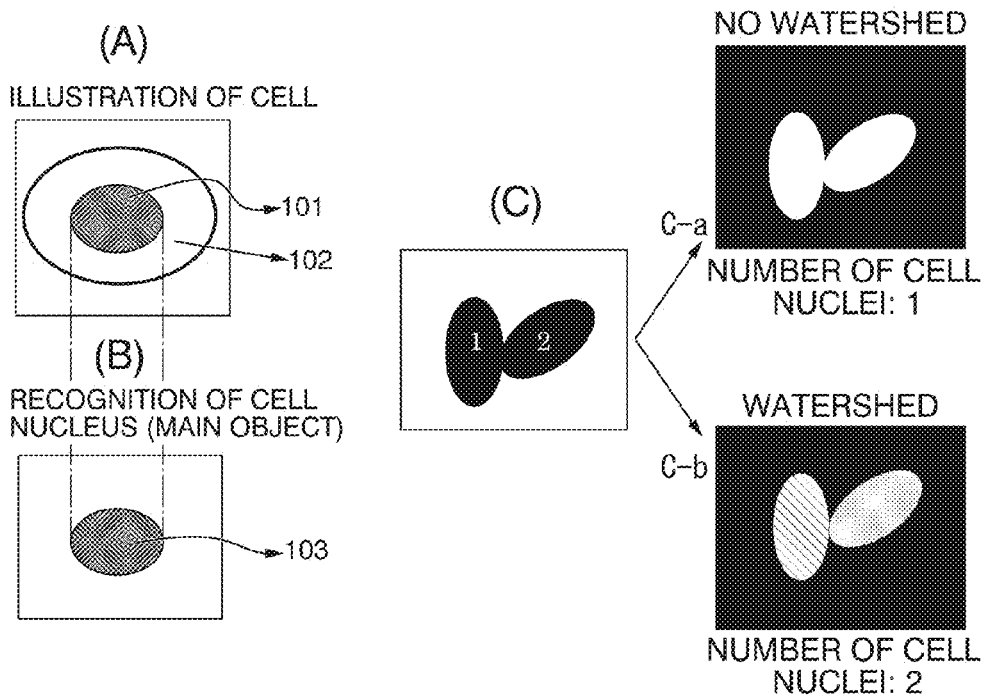
FIGS. 2(A) to 2(C) are diagrams schematically showing a specific method of determining a cell nucleus region in image analysis.

FIGS. 2A to 2C are diagrams schematically showing a specific method of determining a cell nucleus region in image analysis. FIG. 2(A) is a diagram schematically showing one cell. In the drawing, a region 101 represents a region (corresponding to a cell nucleus) of a cell nucleus labeled image labeled by a fluorescent nucleic acid stain, and a region 102 represents the cytoplasm of cells. First, in image analysis, the region 101 of the cell nucleus labeled image, that is, a region which allows a cell nucleus region 103 to be recognized as a main object is set (FIG. 2(B)). Specifically, the maximum value and the minimum value of the area of a portion stained by a fluorescent nucleic acid stain and fluorescence intensity are measured, and a region having an area equal to or greater than the cell nucleus area threshold value from among regions where each pixel has a luminance value equal to or greater than the cell nucleus threshold value is extracted and determined as a cell nucleus region.

When cell density is high and cells are crowded, a watershed algorithm which is known as one region division method is preferably used. According to the watershed algorithm, a region is obtained by spreading the center of the region called a mark to adjacent pixels, and the function is used simultaneously to set such that an individual cell nucleus is recognized (FIG. 2(C)). As shown in FIG. 2(C), when the watershed function is not used, two superimposing cell nuclei are recognized as one cell nucleus (FIG. 2(C) (C-a)). Meanwhile, with the use of the watershed function, two superimposing cell nuclei can be recognized as two cell nuclei (FIG. 2(C) (C-b)). Similarly, a cell nucleus can be recognized through edge recognition or recognition of a constriction of adjacent cells.

A cell bottom reference cross section as a reference for determining a cell region may be each planar tomographic fluorescent labeled image acquired in the step (b). For example, a cell region may be determined in the following manner. First, for the cells to be analyzed in the cell nucleus labeled image of each planar tomographic fluorescent labeled image acquired in the step (b), a total luminance value per image is measured. Next, a planar tomographic fluorescent labeled image in which there are no cell nuclei of cells to be analyzed and which has a cross section having the smallest height from the bottom of the laminated structure is specified as a cell-free cross section. Usually, since there are no cells at the bottom of the laminated structure, it is preferable that a planar tomographic fluorescent labeled image having the smallest height is specified as a cell-free cross section. A cross section which is located above the cell-free cross section, is a planar tomographic fluorescent labeled image having the total luminance value of the cells to be analyzed per image of the cell nucleus labeled image 10 to 50%, preferably, 15 to 40% greater than the cell-free cross section, and is closest to the cell-free cross section is specified as a cell bottom reference cross section.

After the step (d), in the step (e), one planar stacked image is produced for each divided cell region. A method which produces one planar stacked image from a cell region is not particularly limited, and a known image analysis method in which the dimension of a three-dimensional image is reduced to obtain a planar image may be used. For example, for all pixels in one cell region, positional information of the Z axis (the height direction of the three-dimensional tomographic image) is discarded, and all luminance values of pixels at the same positions of the X axis and the Y axis are totaled, thereby producing one planar stacked image.

In the analysis method of the invention, the steps (b) to (e) can be analyzed using one image analysis apparatus which can implement these steps. As the image analysis apparatus, for example, an apparatus in which a confocal laser microscope or the like including imaging means for capturing an image while relatively moving the objective lens and the laminated structure in the direction perpendicular to the optical axis is combined in a known image analysis apparatus, which is generally used in the field of image analysis or an apparatus which is appropriately modified from the image analysis apparatus, may be used.

Specifically, the planar tomographic fluorescent labeled images of the fluorescent labeled laminated structure are sequentially captured by the confocal laser microscope while relatively moving the objective lens and the laminated structure in the direction perpendicular to the optical axis, and image analysis by the image analysis apparatus is automatically performed on image data of each captured planar tomographic fluorescent labeled image, and the construction of the three-dimensional tomographic image, the determination of the cell regions, and the production of one planar stacked image per cell region are performed. Specifically, the cell nucleus region is determined on the basis of the cell nucleus labeled image, and the cell nuclei of the cells to be analyzed in each planar tomographic fluorescent labeled image are measured. Next, a planar tomographic fluorescent labeled image (preferably, the bottom of the laminated structure or a neighboring planar tomographic fluorescent labeled image) in which there are no cell nuclei of the cell to be analyzed and which has the smallest height is specified as a cell-free cross section. A cross section which is located above the cell-free cross section, is a planar tomographic fluorescent labeled image having the total luminance value of the cells to be analyzed per image of the cell nucleus labeled image 10 to 50%, preferably, 15 to 40% greater than the cell-free cross section, and is closest to the cell-free cross section is specified as a cell bottom reference cross section. The obtained planar tomographic fluorescent labeled images are superimposed to construct a three-dimensional tomographic image, and in the three-dimensional tomographic image, a region from a cross section 5 to 10 μm below the cell bottom reference cross section in the height direction of the three-dimensional tomographic image to a cross section 15 to 25 μm above the cell bottom reference cross section in the height direction is determined as a cell region having a cell layer of cells to be analyzed. Then, one planar stacked image per cell region is produced.

In the step (f), image analysis is performed on each produced planar stacked image to analyze the cells in the laminated structure. Image analysis on each planar stacked image can be performed by appropriately combining known image analysis methods. In basic cell image analysis or automatic cell recognition, the determination of a labeled region in the planar stacked image is done by setting a threshold value of luminance suitable for an image. For example, binarization is performed such that points (pixel) at which the luminance value is greater than the set threshold value are represented by 1 and other points are represented by 0, and a region having pixels of 1 is individually divided (individual islands are divided and numbered), thereby recognizing individual fluorescent labeled cell nuclei or biomolecules.

In the step (f), all produced planar stacked images may be subjected to image analysis, or only a part of the planar stacked images may be subjected to analysis. In order to obtain an analysis result with higher precision, it is preferable that a wider region of planar stacked images is subjected to analysis, and it is more preferable that all planar stacked images are subjected to image analysis.

The type of image analysis in the step (f) is not particularly limited. The planar stacked image can be divided into the cell nucleus labeled image and the labeled images of various biomolecules fluorescently labeled in the step (a). Image analysis is performed on each labeled image, thereby obtaining information regarding the form of each fluorescent labeled biomolecule or cell nucleus, the expression level in the cells, the localization in cells, and the like.

For example, the cell nucleus labeled image of the planar stacked image is analyzed, thereby examining the shape or size (area) of the cell nucleus of each cell in the planar stacked image. Specifically, the cell nucleus region in the cell nucleus labeled image is determined. The cell nucleus region can be determined in the same manner as described above. For each cell nucleus region, the average luminance value per pixel in the cell nucleus region, the sum of the luminance values of all pixels in the cell nucleus region, the total area of the pixels in the cell nucleus region, and the shape (total circumference or the like) of the cell nucleus region are measured, and the shape or size of each cell region can be analyzed on the basis of the measured values.

For example, stem cells generally have a cell nucleus smaller than cells after differentiation. In particular, in the case of epithelial cells, stem cells have the smallest cell nucleus, and as the degree of differentiation becomes higher, the cell nucleus tends to increase in size. For this reason, by examining the size of the cell nucleus of each cell in the planar stacked image, it is possible to analyze whether the cells in the planar stacked image are stem cells or differentiated cells.

In regard to the labeled images of the biomolecules, similarly to the cell nucleus labeled image, it is preferable that noise at the time of labeling is excluded, and a threshold value for recognizing the presence/absence of labeling is provided. Since the threshold value varies depending on the types of biomolecules or labeling methods, a biomolecule threshold value is set for each type of biomolecules and each type of labeling methods. For example, after the same type of cells as the cells to be analyzed are stained in advance, and the labeled images of the biomolecules are acquired, the luminance values or area values of the biomolecule regions can be measured from the labeled images, and the threshold value can be set on the basis of the measured values. For example, the luminance value per pixel of a region (background) in each of the labeled images of the biomolecules where it is clear that there are no biomolecules or a statistical value may be the biomolecule threshold value, or a threshold value which is acquired empirically may be used.

For example, the measurement of the abundance, localization, form, and the like of the biomolecules is performed in the following manner. First, the luminance value of each pixel of each labeled image is measured. The measured value is compared with a threshold value determined in advance, and a region (a group of pixels) having a luminance value per pixel equal to or greater than the threshold value is determined as a biomolecule stained region. The average luminance value per pixel of each determined biomolecule stained region, the sum of the luminance values of all pixels in the biomolecule stained region, the total area of the biomolecule stained region, the shape of the biomolecule stained region are appropriately combined and analyzed.

The image analysis method of the invention is suitable for analysis of a laminated structure for transplantation including stem cells in which the positional relationship between cells is important since cells in a laminated structure including a cell layer can be analyzed while maintaining the laminated structure.

(Method of Evaluating Laminated Structure for Corneal Transplantation)

In a method of evaluating a laminated structure for corneal transplantation of the invention (hereinafter, referred to as an evaluation method of the invention), the evaluation of a laminated structure which is formed by culturing epithelial stem cells and used for corneal transplantation is performed using the image analysis method of the invention. A laminated structure for corneal transplantation to be evaluated by the evaluation method of the invention is not particularly limited insofar as a laminated structure includes cultured epithelial stem cells and is transplanted to a cornea, and a laminated structure which is produced by any known method may be used.

Specifically, the evaluation method of the invention includes the steps of:

(a') fluorescently labeling a cell nucleus in the laminated structure and one or more types of biomolecules selected from a group including biomolecules specific to epithelial stem cells, biomolecules specific to epithelial cells after differentiation or a surrounding tissue, and biomolecules in both the epithelial stem cells and the epithelial cell after differentiation;

(b') acquiring a plurality of planar tomographic fluorescent labeled images in different height directions from the laminated structure for each type of fluorescently labeled biomolecules after the step (a');

(c') superimposing a planar tomographic fluorescent labeled image group acquired in the step (b') to construct a three-dimensional tomographic image;

(d') dividing the three-dimensional tomographic image constructed in the step (c') into a lower cell region of a cell layer including epithelial stem cells and an upper cell region above and adjacent to the lower cell region;

(e') producing one planar stacked image for each divided region after the step (d); and (f') performing image analysis on each planar stacked image produced in the step (e') and evaluating the laminated structure on the basis of the obtained analysis result, The steps (a') to (c') can be performed in the same manner as the steps (a) to (c) except that one or more types of biomolecules selected from a group including biomolecules specific to epithelial stem cells, biomolecules specific to epithelial cells after differentiation, or a surrounding tissue, and biomolecules in both the epithelial stem cells and the epithelial cells after differentiation are fluorescently labeled.

As the biomolecules specific to the epithelial stem cells, p63 which is expressed to be comparatively specific to cell nuclei of the stem cells may be used. As the biomolecules specific to the epithelial cells after differentiation, epithelial cytokeratin, such as AE5, and mucin, such as MUC16, may be used. As the biomolecules specific to a surrounding tissue of the epithelial cells after differentiation, biomolecules, such as ZO-1, which constitute the tight junction of the epithelial cells may be used. As the biomolecules in both the epithelial stem cells and the epithelial cells after differentiation, cytokeratin, such as panCK, may be used.

In the invention, it is preferable that at least one of biomolecules to be fluorescently labeled is a biomolecule specific to the epithelial stem cells or a biomolecule specific to the epithelial cells after differentiation or the surrounding tissue. By analyzing the expression level, localization, and the like in the cells of the biomolecules, it is possible to identify whether the fluorescent labeled cells are epithelial stem cells or differentiated epithelial cells.

As the biomolecules to be fluorescently labeled, one or more types selected from a group including AE5, MUC16, ZO-1, panCK, and p63 are preferably used. When fluorescently labeling panCK, it is preferable that one or more types selected from a group including AE5, MUC16, ZO-1, and p63 are fluorescently labeled.

In the step (d'), a lower cell region of a cell layer including epithelial stem cells and an upper cell region above and adjacent to the lower cell region are divided from the constructed three-dimensional tomographic image. The determination of the lower cell region and the upper cell region can be performed in the same manner as when epithelial stem cells are cells to be analyzed in the step (d).

In the invention, in the step (d'), it is preferable that the constructed three-dimensional tomographic image is divided into two cell regions of a lower cell region of a cell layer including epithelial stem cells and an upper cell region above and adjacent to the lower cell region. Specifically, the lower cell region and the upper cell region are determined by the steps of (i') specifying, as a cell-free cross section, a cross section, in which there are no cell nuclei and which has the smallest height from the bottom of the laminated structure, from among cross sections parallel to the bottom of the three-dimensional tomographic image, (ii') specifying, as a stem cell bottom reference cross section, a cross section which is located above the cell-free cross section, has a total luminance value per image of the cell nucleus labeled image 10 to 50% greater than the cell-free cross section, and is closest to the cell-free cross section, from among the cross sections parallel to the bottom of the three-dimensional tomographic image, and (iii') determining, as the lower cell region, a region from a cross section 5 to 10 µm below the stem cell bottom reference cross section in the height direction of the laminated structure to a cross section 15 to 25 µm above in the height direction of the laminated structure.

The lower cell region and the upper cell region may be determined by the steps of (i"-1) specifying, as a lower cell-free cross section, a cross section, in which there are no cell nuclei and which has the smallest height from the bottom of the laminated structure, from among cross sections parallel to the bottom of the three-dimensional tomographic image, (i"-2) specifying, as an upper cell-free cross section, a cross section, in which there are no cell nuclei and which has the greatest height from the bottom of the laminated structure, from among the cross sections parallel to the bottom of the three-dimensional tomographic image, and (iii") defining a cross section at the same distance from both the lower cell-free cross section and the upper cell-free cross section as an interface, determining a region from the lower cell-free cross section to the interface as a lower cell region, and determining a region from the interface to the upper cell-free cross section as an upper cell region.

According to the determination method, substantially the middle surface of a region including the cells in the laminated structure constantly becomes a division surface of the lower cell region and the upper cell region.

Figure 3:
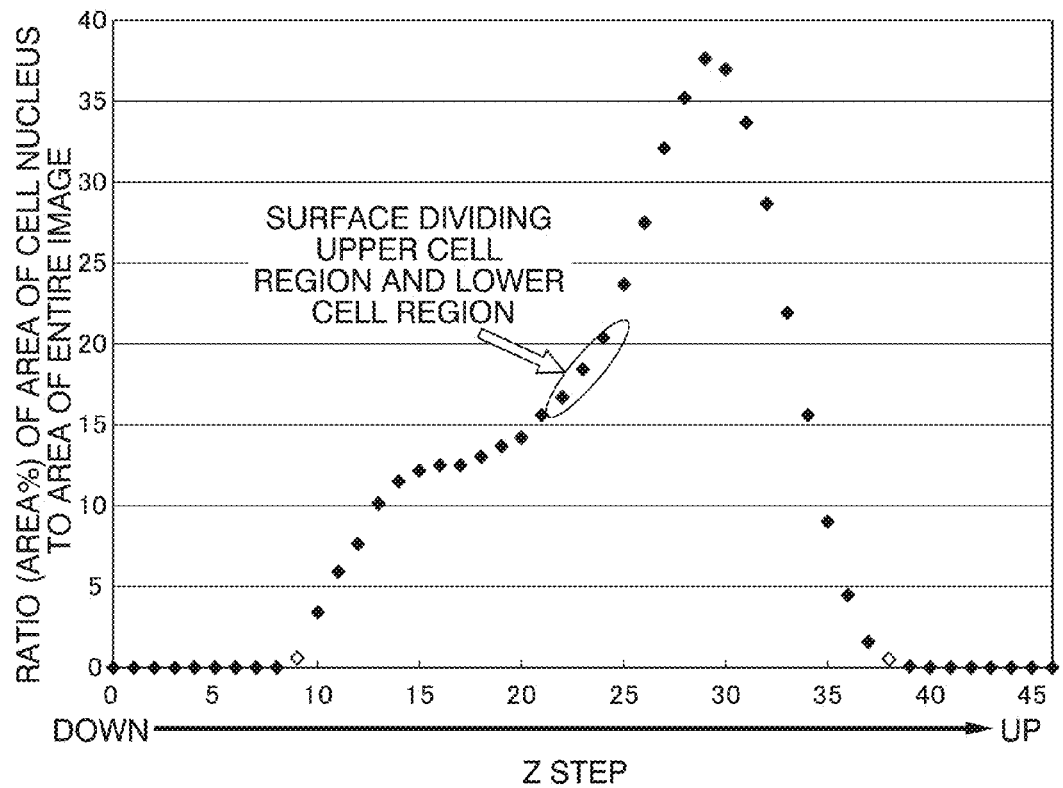
FIG. 3 is a diagram showing an example of a result of measuring a ratio (AREA %; vertical axis) of a cell nucleus area with respect to an entire image at each height (Z axis) (step; horizontal axis) from the bottom for a planar tomographic fluorescent labeled image (cell nucleus labeled image) which is acquired from a laminated structure for corneal transplantation formed by culturing epithelial stem cells.

FIG. 3 shows an example of a result of measuring a ratio (AREA %) of a cell nucleus area with respect to an entire image for each cell nucleus labeled image when a cell nucleus in a laminated structure for corneal transplantation formed by culturing epithelial stem cells is fluorescently stained, and then planar tomographic fluorescent labeled images (cell nucleus labeled images) in different height directions are acquired from the laminated structure for corneal transplantation. The vertical axis represents the ratio (AREA %) of the cell nucleus area with respect to the entire image, and the horizontal axis represents the height (Z axis; step) from the bottom of the cell nucleus labeled image. The cell nucleus is measured using cell nucleus labeled images from 9 step to 38 step. That is, in the laminated structure for corneal transplantation, a cell nucleus labeled image of 8 step is a lower cell-free cross section, a cell nucleus labeled image of 39 step is an upper cell-free cross section, and the middle surface (that is, the division surface of the lower cell region and the upper cell region) becomes a cross section parallel to the bottom at height of 23.5 step. Near the division surface determined in the above-described manner, the ratio of the cell nucleus area with respect to the entire image changes largely. This is because stem cells are primarily located below the division surface, and cells (that is, differentiated cells) having different properties from the cells on the lower side are located above the division surface. Actually, when a lower cell region where a comparatively small cell group is located and an upper cell region where a comparatively large cell group is located are visually divided from the three-dimensional tomographic image of the laminated structure for corneal transplantation, the division surface of the lower cell region and the upper cell region has height of 22 to 24 step (a place indicated by an arrow in FIG. 3). From this result, it is clear that a method of determining the upper cell region and the lower cell region in the laminated structure for corneal transplantation by the steps (i"-1), (i"-2), and (iii") is appropriate.

Of course, even if three or more cell regions to be analyzed are divided from the three-dimensional tomographic image, the laminated structure for corneal transplantation can be evaluated. However, as the evaluation method of the invention, even if the three-dimensional tomographic image is divided into two cell regions of a cell region including epithelial stem cells and a cell region including differentiated epithelial cells, the laminated structure for corneal transplantation can be sufficiently evaluated. In this case, since the determination reference of the evaluation is simple compared to a case where the three-dimensional tomographic image is divided into three or more cell regions, clear and reliable evaluation can be performed efficiently.

Image analysis in the steps (e') and (f') can be performed in the same manner as the steps (e) and (f).

As a result of image analysis, when it is found that cells in a planar stacked image (hereinafter, referred to as a lower planar stacked image) produced from the lower cell region are stem cells and cells in a planar stacked image (hereinafter, referred to as an upper planar stacked image) produced from the upper cell region are differentiated epithelial cells, it is evaluated that the laminated structure for corneal transplantation served for analysis is normal and suitable for corneal transplantation.

AE5 is a type of cytokeratin, and epithelial tissue ceratin is stained by fluorescently labeling AE5. For this reason, in a normal laminated structure for corneal transplantation, cells in the upper planar stacked image have a higher expression level than cells in the lower planar stacked image. Accordingly, in the step (a'), when at least the cell nucleus and AE5 are fluorescently labeled, and when the average luminance value per pixel in a fluorescent labeled image of AE5 of the upper planar stacked image, the sum of the luminance values of all pixels, and the total area of pixels having a luminance value per pixel equal to or greater than a threshold value are greater than a fluorescent labeled image of AE5 of the lower planar stacked image, or when the ratio of pixels having a luminance value per pixel equal to or greater than the threshold value in the upper planar stacked image is equal to or greater than 50%, it is evaluated that the laminated structure for corneal transplantation served for analysis is suitable for corneal transplantation. To the contrary, when the average luminance value per pixel in the fluorescent labeled image of AE5 of the lower planar stacked image, the sum of the luminance values of all pixels, and the total area of pixels having a luminance value per pixel equal to or greater than the threshold value are greater than the upper planar stacked image, or when the ratio of pixels having a luminance value per pixel in the upper planar stacked image is equal to or greater than the threshold value smaller than 50%, it is evaluated that the laminated structure for corneal transplantation is not suitable for corneal transplantation.

MUC16 is a type of mucin, and for this reason, in a normal laminated structure for corneal transplantation, expression is rarely observed in the cells of the lower planar stacked image, and the expression level in the cells in the upper planar stacked image or a neighboring region becomes higher. Accordingly, in the step (a'), when at least the cell nucleus and MUC16 are fluorescently labeled, and when the average luminance value per pixel in a fluorescent labeled image of MUC16 of the upper planar stacked image, the sum of the luminance values of all pixels, and the total area of pixels having a luminance value per pixel equal to or greater than a threshold value are greater than a fluorescent labeled image of MUC16 of the lower planar stacked image, it is evaluated that the laminated structure for corneal transplantation served for analysis is suitable for corneal transplantation. To the contrary, when there is no difference in the average luminance value per pixel in the fluorescent labeled image of MUC16, the sum of the luminance values of all pixels, and the total area of pixels having a luminance value per pixel equal to or greater than the threshold value between the upper planar stacked image and the lower planar stacked image or when the values of the lower planar stacked image are greater than those of the upper planar stacked image, it is evaluated that the laminated structure for corneal transplantation is not suitable for corneal transplantation.

ZO-1 is a tight junction marker between epithelial cells, and for this reason, in a normal laminated structure for corneal transplantation, expression is rarely observed in the cells in the lower planar stacked image, and in the upper planar stacked image, expression is observed in the shape of a network structure. Accordingly, in the step (a'), when at least the cell nucleus and ZO-1 are fluorescently labeled, and when the average luminance value per pixel in a fluorescent labeled image of ZO-1 of the upper planar stacked image, the sum of the luminance values of all pixels, and the total area of pixels having a luminance value per pixel equal to or greater than a threshold value are greater than a fluorescent labeled image of ZO-1 of the lower planar stacked image, and a region of pixels having the luminance value per pixel in the fluorescent labeled of ZO-1 of the upper planar stacked image equal to or greater than the threshold value has a shape of a network structure, it is evaluated that the laminated structure for corneal transplantation served for analysis is suitable for corneal transplantation. To the contrary, when a network structure is observed in the fluorescent labeled image of ZO-1 of the lower planar stacked image, it is evaluated that the laminated structure for corneal transplantation is not suitable for corneal transplantation.

Since the tight junction of epithelial cells has a network structure, for example, even if a thin-layer section of a cross section perpendicular to the bottom is obtained from the laminated structure for corneal transplantation and ZO-1 in the thin-layer section is fluorescently labeled, a network structure cannot be observed on the section, and it is not possible to know whether or not the tight junction of epithelial cells is formed in the upper cell region of the laminated structure for corneal transplantation. The evaluation method of the invention uses the analysis method of the invention, thereby determining the presence/absence of the tight junction of epithelial cells and performing evaluation. A network structure in a planar stacked image can be detected by known image analysis means, such as a string detection method which detects a filamentous network structure or a stone detection method which detects one network structure as a stone pavement.

A large amount of p63 is primarily located in the cell nuclei of stem cells, and for this reason, in a normal laminated structure for corneal transplantation, a larger amount of p63 is clearly observed in the cells in the lower planar stacked image than the cells in the upper planar stacked image. Accordingly, in the step (a'), when at least the cell nucleus and p63 are fluorescently labeled, and when the average luminance value per pixel of each cell nucleus region in a labeled image of p63 of the upper planar stacked image is greater than a fluorescent labeled image of p63 of the lower planar stacked image, it is evaluated that the laminated structure for corneal transplantation served for analysis is suitable for corneal transplantation. To the contrary, when the average luminance value per pixel in the fluorescent labeled image of p63 is greater in the lower planar stacked image than the upper planar stacked image or substantially the same, it is evaluated that the laminated structure for corneal transplantation is not suitable for corneal transplantation.

panCK is cytokeratin which is widely located in epithelial cells regardless of the presence/absence of differentiation or the degree of differentiation, and in a normal laminated structure for corneal transplantation, expression is observed in the cytoplasm of both the cells in the lower planar stacked image and the cells in the upper planar stacked image. For this reason, in the step (a'), when panCK is fluorescently labeled, and when the average luminance value per pixel in each cytoplasmic region of a labeled image of panCK of the upper planar stacked image is substantially the same as a fluorescent labeled image of panCK of the lower planar stacked image, it is evaluated that the laminated structure for corneal transplantation served for analysis is suitable for corneal transplantation. To the contrary, when the average luminance value per pixel in a cytoplasmic region of a labeled image of panCK significantly differs between the upper planar stacked image and the lower planar stacked image, it is evaluated that the laminated structure for corneal transplantation is suitable for corneal transplantation.

The cytoplasmic region may be measured by any known method in the field of image analysis of cells. The determination of a cytoplasmic region from a cell nucleus labeled image can be done by, for example, a method or the like described in Japanese Unexamined Patent Application, First Publication No. 2011-75278.

Specifically, a region which is a doughnut-shaped region with the outer circumferential portion of the determined cell nucleus region as the inner circumference and in which the width of the doughnut shape (the shortest distance (that is, the width) from each point on the outer circumference of the region to the inner circumference is identical at all points on the outer circumference) has a regular interval can be determined as a cytoplasmic region. When creating a cytoplasmic region, it is possible to freely set the width of the doughnut shape (the distance between the outer circumferential portion and the inner circumferential portion of the cell nucleus region). For example, a labeled image in which the cell membrane of cells and nucleic acid for use in analysis may be acquired in advance, the distance between the outer circumference of the cell nucleus to the cell membrane may be measured, and the width (thickness) of the cytoplasmic region may be determined on the basis of the measured value. In general, since the thickness of the cytoplasm of cells is substantially identical regardless of the types of cells or the like, the distance from the outer circumference of the cell nucleus region to the outer circumference of the cytoplasmic region may be set to about 10 to 30 pixels.

In the step (a'), the cytoplasm of cells may be separately labeled, and in the step (b'), a labeled image of the labeled cytoplasm of cells may be acquired, and the cytoplasmic region may be determined on the basis of the acquired labeled image of the cytoplasm of cells. A method of labeling the cytoplasm of cells is not particularly limited insofar as nucleic acid or biomolecules to be analyzed are labeled so as to allow visual distinction on a captured image, and any known method in the art may be used.

Figure 4:
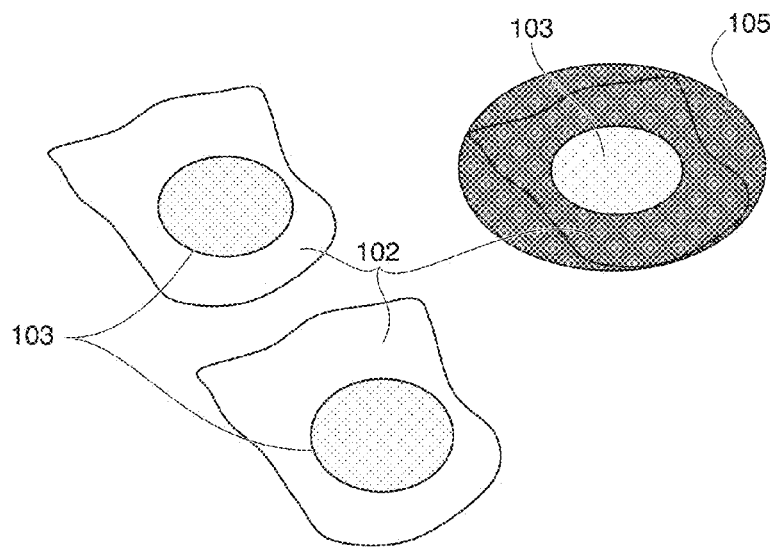
FIG. 4 is a diagram schematically showing a specific method of determining a cytoplasmic region in image analysis.

FIG. 4 is a diagram schematically a specific method of determining a cytoplasmic region in image analysis. In FIG. 4, a region 103 represents a cell nucleus region, a region 102 represents the cytoplasm of cells, and a region 105 represents a cytoplasmic region. As shown in FIG. 4, the cytoplasm of cells is included without leakage, and a doughnut-shaped region in which a cell nucleus region is removed is set as a cytoplasmic region.

As described above, in the case of epithelial cells, stem cells have the smallest cell nucleus, and as the degree of differentiation becomes high, the cell nucleus tends to increase in size. For example, in the planar images of cells, the cell nuclei of large cells from among differentiated cells have an area three to six times greater than epithelial stem cells. For this reason, when the average value of the area of the cell nucleus region in the upper planar stacked image is three times greater than the average value of the area of the cell nucleus region in the lower planar stacked image, it is evaluated that the laminated structure for corneal transplantation served for analysis is suitable for corneal transplantation. To the contrary, when the average value of the area of the cell nucleus region in the upper planar stacked image is substantially the same as the lower planar stacked image, it is evaluated that the laminated structure for corneal transplantation is not suitable for corneal transplantation.

A threshold value of the area of the cell nucleus for identifying differentiated cells and stem cells is provided in advance, and when the ratio of the cell nucleus region having an area equal to or greater than the threshold value to all cell nucleus regions in the upper planar stacked image is greater than the lower planar stacked image, it may be evaluated that the laminated structure for corneal transplantation served for analysis is suitable for corneal transplantation. For example, epithelial stem cells and differentiated epithelial cells can be stained using a fluorescent nucleic acid stain in advance to acquire cell nucleus labeled images, then the area value of the cell nucleus in the cell nucleus labeled image can be measured, and the threshold value can be set on the basis of the measured value.

EXAMPLES

Next, although the invention will be described in detail in connection with the following examples, the invention is not limited to the following examples.

(Laminated Structure for Corneal Transplantation)

Unless particularly described, a laminated structure for corneal transplantation analyzed in the following examples was produced in the following manner. First, human corneal epithelial tissues were isolated from a corneoscleral limbus isolated from a cornea of a cadaveric donor (provided by Northwest Lions Eye Bank (Seattle, Wash.)) using scissors (n=4). Human oral mucosal tissues (3×3 mm samples) were surgically excised from a buccal mucosa inside an oral cavity of a healthy volunteer under anesthesia using xylocalne (n=3). Each tissue was cleaned with Dulbecco's phosphate buffered saline (PBS) containing an antibiotic and an antifungal agent and was incubated with Dispase II at 37° C. for an hour. The isolated epithelial layer was treated with a trypsin-ethylenediaminetetraacetic acid (EDTA) solution (manufactured by Invitrogen). Then, the suspended cells were seeded into a temperature-sensitive culture insert (manufactured by CellSeed) along with mitomycin C-treated NIH/3T3 cells isolated by a cell culture insert such that the initial cell density was $1.5 \times 10^5$ cells (corneal epithelial cells) or $2.0 \times 10^5$ cells (oral mucosal epithelial cells)/23-mm insert, and were cultured in keratinocyte culture medium (KCM). The KCM is a Dulbecco's modified Eagle's medium (DMEM)/F12 (mixing ratio=3:1) to which 10% of fetal calf serum (manufactured by Japan Bio Serum), 0.5% of insulin-transferrin-selenium (ITS, manufactured by Invitrogen Corporation), 10 μM of isoproterenol (manufactured by Kowa), $2.0 \times 10^{-9}$ M of triiodothyronine (manufactured by MP Biomedicals), 0.4 lag/mL of hydrocortisone succinate (manufactured by Wako Pure Chemical), and 10 ng/mL of EGF (manufactured by R&D Systems) were added. In the following examples, the step of fluorescently labeling the obtained laminated structure for corneal transplantation was completed during the day on which cell culturing ended.

Example 1

The cell nucleus and AE5 of the laminated structure for corneal transplantation were fluorescently labeled, and evaluation was performed by the evaluation method of the invention.

First, the cell nucleus and AE5 of the laminated structure for corneal transplantation were fluorescently labeled. In fluorescent labeling of AE5, an unlabeled anti-AE5 antibody (manufactured by PROGEN, Product Number: 61807) or an anti-AE5 antibody (Alexa488 labeled anti-AE5 antibody) directly labeled with Alexa488 in advance was used. The labeling of Alexa488 to an anti-AE5 antibody was performed using a monoclonal antibody labeling kit (manufactured by Invitrogen, Product Number: A20181).

Specifically, the prepared cell sheet (a cell sheet removed from a membrane or a cell sheet with a membrane attached thereto) was cleaned with PBS (-) or a tris buffer solution (TBS), fixed with cold 100% methanol for ten minutes, and cleaned with PBS (-) or a tris buffer solution (TBS). Next, the unlabeled anti-AE5 antibody or the Alexa488 labeled anti-AE5 antibody was added, and reaction was made at room temperature for 40 minutes to 60 minutes (staining buffer: TBS containing 0.3% tritonX-100 and 5% donkey serum (manufactured by Sigma, product No.: D9663)). When the unlabeled anti-AE5 antibody was used, cleaning was performed after the reaction. Then, as a secondary antibody, Alexa488 goat anti-mouse IgG (H+L) antibody was added, and reaction was made at room temperature for 20 minutes to 30 minutes (staining buffer: the same as above). After cleaning, a DAPI (5 μg/mL) solution was added, and reaction was made at room temperature for five minutes. When the Alexa488 labeled anti-AE5 antibody was used, cleaning was performed after the reaction. Then, a DAPI (5 μg/mL) solution was added, and reaction was made at room temperature for five minutes. After the reaction was completed, cleaning was performed, thereby obtaining the laminated structure for corneal transplantation in which the cell nucleus and AE5 were fluorescently labeled.

The fluorescent labeled laminated structure for corneal transplantation was disposed at the bottom of the cell observation container. The cell observation container was installed on a sample installation surface of a confocal laser microscope FV10i (manufactured by Olympus), and images were sequentially captured while relatively moving the objective lens and laminated structure in the direction perpendicular to the optical axis.

Figure 5A:
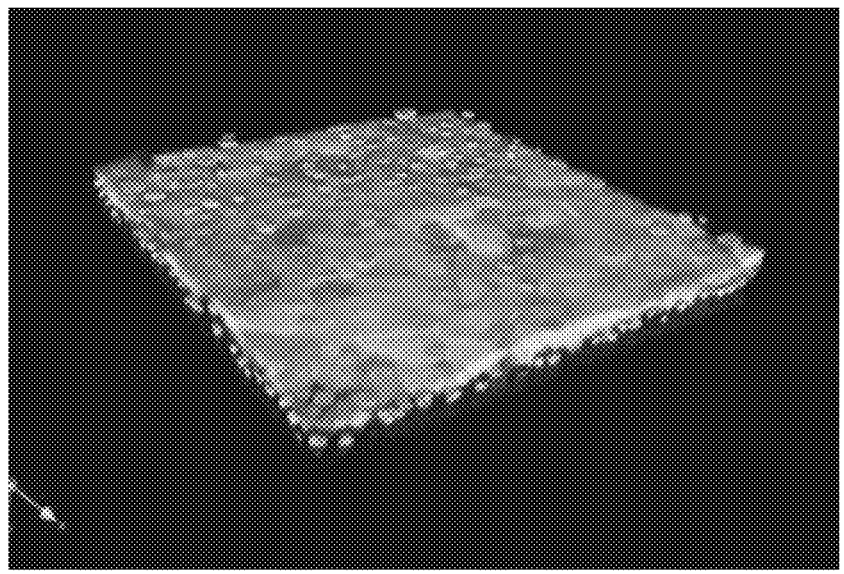
FIGS. 5A to 5C show a three-dimensional tomographic image constructed in Example 1.
Figure 5B:
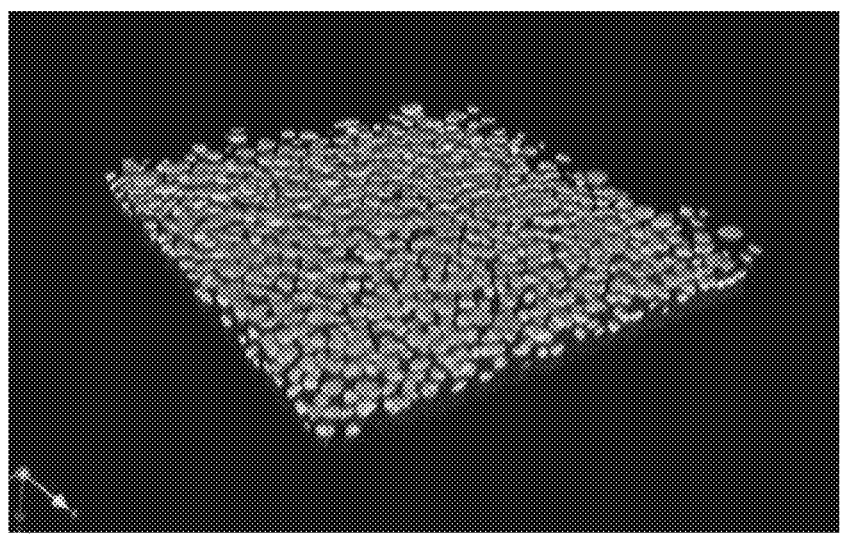
Figure 5C:
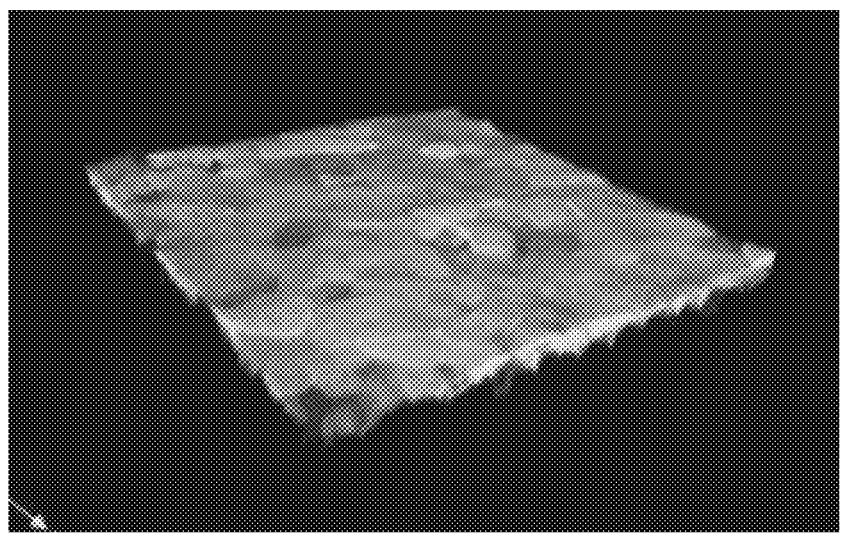

A cell nucleus labeled image and an AE5 labeled image were captured for each microscopic field. The obtained planar image data was superimposed to construct a three-dimensional tomographic image. The cell nucleus labeled image of the constructed three-dimensional tomographic image is shown in FIGS. 5A to 5C. FIG. 5A shows a superimposition image of a cell nucleus labeled image and an AE5 labeled image, FIG. 5B shows a cell nucleus labeled image, and FIG. 5C shows an AE5 labeled image. As a result, a large number of cells having a comparatively small cell nucleus were located on the lower side of the three-dimensional tomographic image, and cells having a comparatively large cell nucleus were located on the upper side at a lower density than the lower side. A lower cell region having a comparatively small cell group and an upper cell region having a comparatively large cell group were visually divided from the three-dimensional tomographic image, and one planar stacked image was produced for each cell region. The construction of the three-dimensional tomographic image from planar image data and the production of the planar stacked image were performed using FV10i software (manufactured by Olympus).

Figure 6:
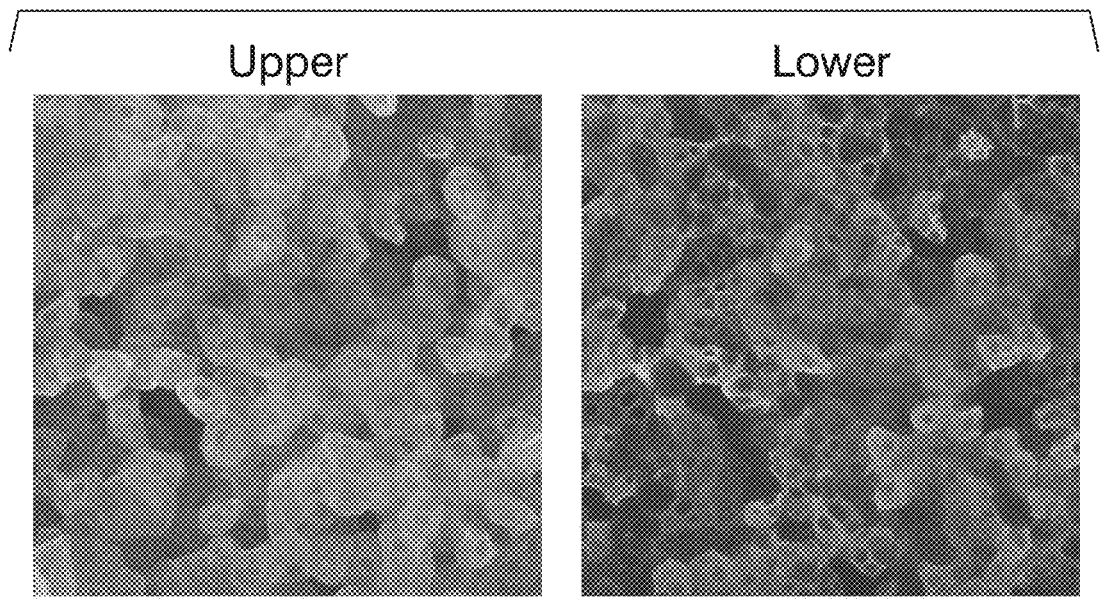
FIG. 6 shows AE5 labeled images of an upper planar stacked image and a lower planar stacked image in Example 1.

FIG. 6 shows AE5 labeled images of an upper planar stacked image and a lower planar stacked image. As a result, while a large number of cells were fluorescently labeled in the upper planar stacked image, in the lower planar stacked image, less cells was labeled than the upper planar stacked image. For the obtained upper planar stacked image and the lower planar stacked image, the sum (total luminance value) of the luminance values of all pixels per image of the AE5 labeled image, the average luminance value per pixel, and the total area of pixels having a luminance value per pixel equal to or greater than a threshold value were measured. Table 1 shows the measurement results of the total luminance value per image of the upper planar stacked image and the lower planar stacked image, the average luminance value per pixel, the total area of the pixels having a luminance value per pixel equal to or greater than the threshold value, and the ratio (%) of the pixels having a luminance value per pixel equal to or greater than the threshold value per image. In Table 1 and FIG. 6, "Upper" represents the result of the upper planar stacked image, and "Lower" represents the result of the lower planar stacked image. As a result, the average luminance value per pixel in the fluorescent labeled image of AE5 of the upper planar stacked image, the sum of the luminance values of all pixels, and the total area of pixels having a luminance value per pixel equal to or greater than the threshold value were greater than the fluorescent labeled image of AE5 of the lower planar stacked image.

The ratio of the pixels having a luminance value per pixel equal to or greater than the threshold value in the fluorescent labeled image of AE5 of the upper planar stacked image was equal to or greater than 50%. Therefore, it was evaluated that the laminated structure for corneal transplantation was normal and suitable for corneal transplantation.

|  | Total luminance value per image | Average luminance value per pixel | Total area of pixels having luminance value per pixel equal to or greater than threshold value | Ratio (%) of pixels having luminance value per pixel equal to or greater than threshold value per image |
|---|---|---|---|---|
| Upper | 778000000 | 1300 | 597000 | 62.8 |
| Lower | 513000000 | 1210 | 423000 | 44.5 |

Example 2

The cell nucleus and MUC16 of the laminated structure for corneal transplantation were fluorescently labeled, and evaluation was performed by the evaluation method of the invention.

First, the cell nucleus and MUC16 of the laminated structure for corneal transplantation were fluorescently labeled. In fluorescent labeling of MUC16, an unlabeled anti-MUC16 antibody (manufactured by Abcam, Product Number: ab693), or an anti-MUC16 antibody (Alexa555 labeled anti-MUC16 antibody) directly labeled by Alexa555 in advance was used. The labeling of Alexa555 to the anti-MUC16 antibody was performed using a Zenon IgG1 labeling kit (manufactured by Invitrogen, Product Number: Z25060).

Specifically, the cell nucleus and MUC16 of the laminated structure for corneal transplantation were fluorescently labeled in the same manner as in Example 1, except that an unlabeled anti-MUC16 antibody, an Alexa555 labeled anti-MUC16 antibody, and an Aleaxa555 goat anti-mouse IgG (H+L) antibody were used, instead of an unlabeled anti-AE5 antibody, an Aleaxa488 labeled anti-AE5 antibody, and an Aleaxa488 goat anti-mouse IgG (H+L) antibody.

Figure 7A:
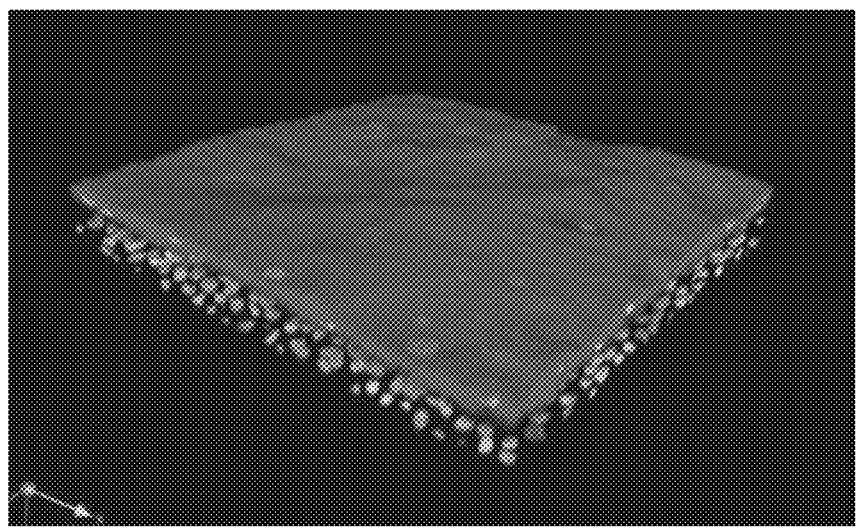
FIGS. 7A to 7C show a three-dimensional tomographic image constructed in Example 2.
Figure 7B:
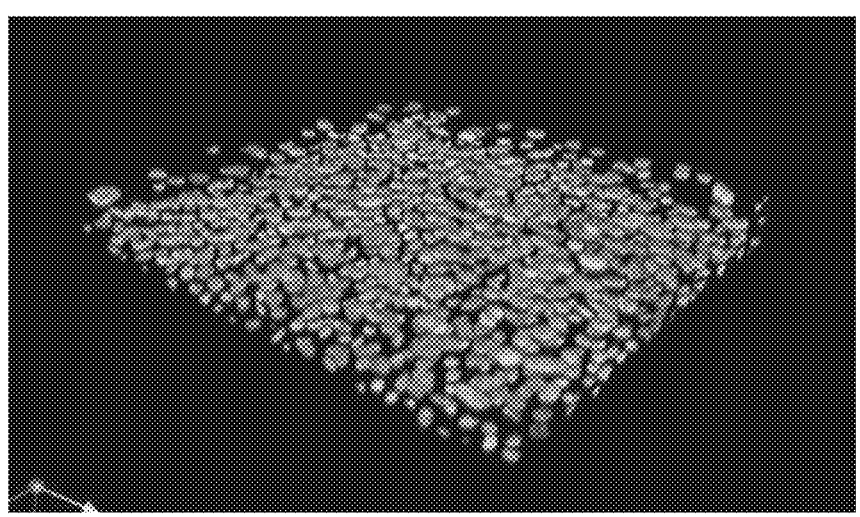
Figure 7C:
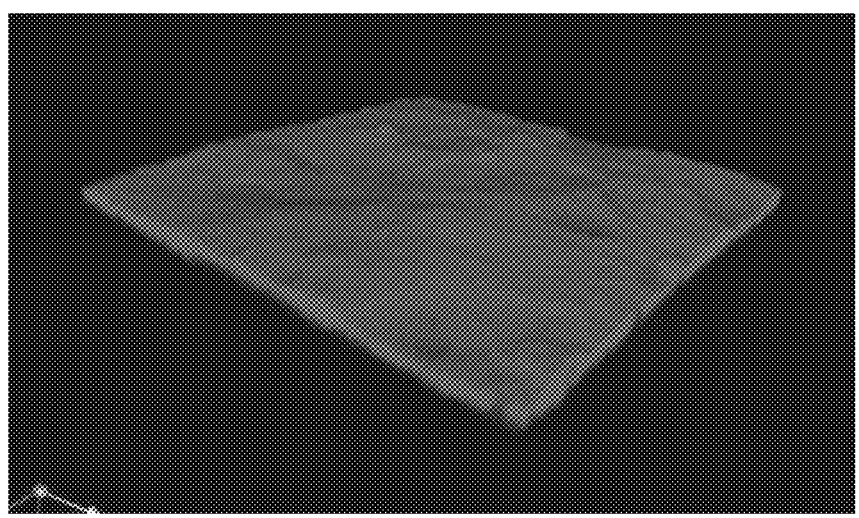

Similarly to Example 1, a cell nucleus labeled image and a MUC16 labeled image of the fluorescent labeled laminated structure for corneal transplantation were captured, and the obtained planar image data was superimposed to construct a three-dimensional tomographic image. The cell nucleus labeled image of the constructed three-dimensional tomographic image is shown in FIGS. 7A to 7C. FIG. 7A shows a superimposition image of a cell nucleus labeled image and a MUC16 labeled image, FIG. 7B shows a cell nucleus labeled image, and FIG. 7C shows a MUC16 labeled image. As a result, a large number of cells having a comparatively small cell nucleus were located on the lower side of the three-dimensional tomographic image, and cells having a comparatively large cell nucleus were located on the upper side at a lower density than the lower side. Similarly to Example 1, the lower cell region and the upper cell region were divided from the three-dimensional tomographic image, and one planar stacked image was produced for each cell region.

Figure 8:
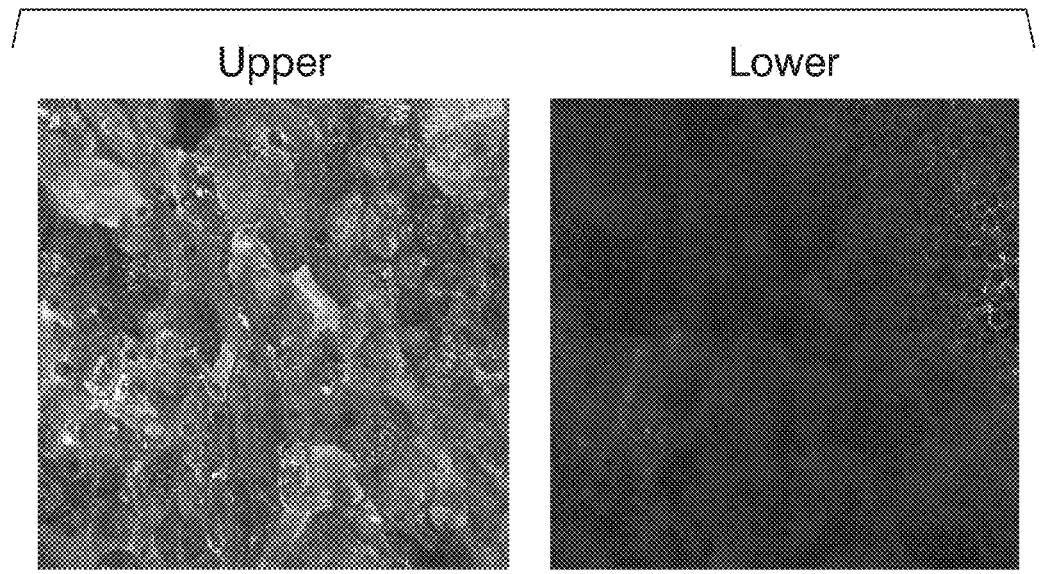
FIG. 8 shows MUC16 labeled images of an upper planar stacked image and a lower planar stacked image in Example 2.

FIG. 8 shows MUC16 labeled images of an upper planar stacked image and a lower planar stacked image. As a result, while a large number of cells were fluorescently labeled in the upper planar stacked image, in the lower planar stacked image, there were no labeled cells. For the obtained upper planar stacked image and lower planar stacked image, the total luminance value per image in the MUC16 labeled image, the average luminance value per pixel, the total area of pixels having a luminance value per pixel equal to or greater than a threshold value, and the ratio (%) of the pixels having a luminance value per pixel equal to or greater than the threshold value per image were measured. The measurement results are shown in Table 2. As a result, no pixels having a luminance value per pixel equal to or greater than the threshold value in the lower planar stacked image were detected, and the average luminance value per pixel in the fluorescent labeled image of MUC16 of the upper planar stacked image and the sum of the luminance values of all pixels were greater than the fluorescent labeled image of MUC16 of the lower planar stacked image. Therefore, it was evaluated that the laminated structure for corneal transplantation was normal and suitable for corneal transplantation.

|  | Total luminance value per image | Average luminance value per pixel | Total area of pixels having luminance value per pixel equal to or greater than threshold value | Ratio (%) of pixels having luminance value per pixel equal to or greater than threshold value per image |
|---|---|---|---|---|
| Upper | 1010000000 | 1590 | 634000 | 66.7 |
| Lower | 0 | 0 | 0 | 0.0 |

Example 3

The cell nucleus and ZO-1 of the laminated structure for corneal transplantation were fluorescently labeled, and evaluation was performed by the evaluation method of the invention.

First, the cell nucleus and ZO-1 of the laminated structure for corneal transplantation were fluorescently labeled. In fluorescent labeling of ZO-1, an unlabeled anti-ZO-1 antibody (manufactured by Invitrogen, Product Number: 339100), or an anti-ZO-1 antibody (biotin labeled anti-ZO-1 antibody) directly labeled with biotin in advance were used. The labeling of biotin to the anti-ZO-1 antibody was performed using Biotin Labeling kit-SH (manufactured by Dojindo).

Specifically, the prepared cell sheet (a cell sheet removed from a membrane or a cell sheet with a membrane attached thereto) was cleaned with PBS (−) or a tris buffer solution (TBS), fixed with cold 100% methanol for ten minutes, and cleaned with PBS (−) or a tris buffer solution (TBS). Next, the unlabeled anti-ZO-1 antibody or the biotin labeled anti-ZO-1 antibody was added, and reaction was made at room temperature for 40 minutes to 60 minutes (staining buffer: TBS containing 0.3% tritonX-100 and 5% donkey serum (manufactured by Sigma, Product Number: D9663)). When the unlabeled anti-ZO-1 antibody was used, cleaning was performed after the reaction. As a secondary antibody, an Alexa555 goat anti-mouse IgG (H+L) antibody was added, and reaction was made at room temperature for 20 minutes to 30 minutes (staining buffer: the same as above). When the biotin labeled anti-ZO-1 antibody was used, cleaning was performed after the reaction. Then, Alexa555 labeled streptavidin was added, and reaction was made at room temperature for 20 minutes to 30 minutes (staining buffer: the same as above). After the reaction was completed, cleaning was performed, thereby obtaining the laminated structure for corneal transplantation in which the cell nucleus and ZO-1 were fluorescently labeled.

Figure 9A:
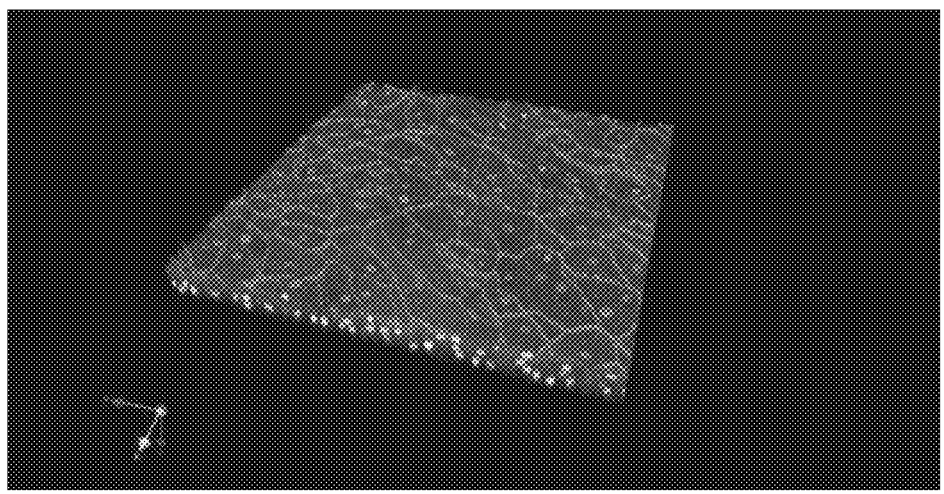
FIGS. 9A to 9C show a three-dimensional tomographic image constructed in Example 3.
Figure 9B:
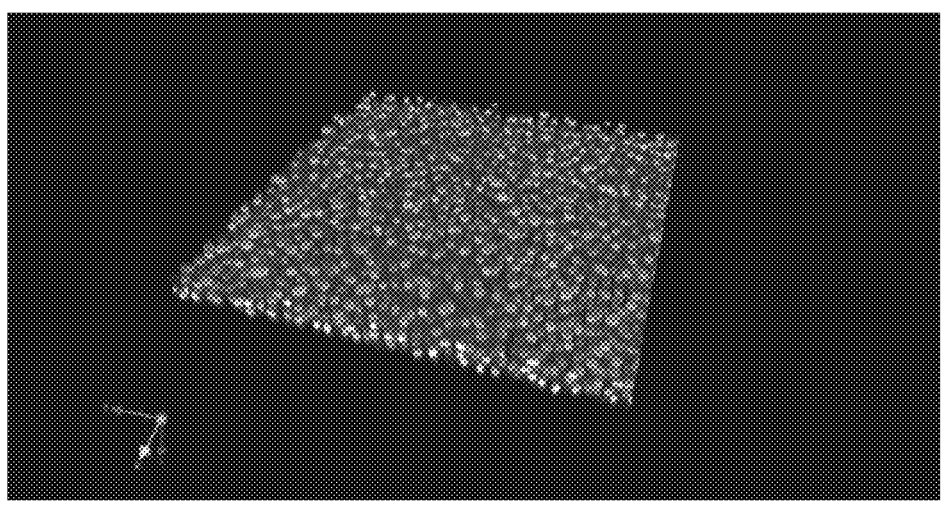
Figure 9C:
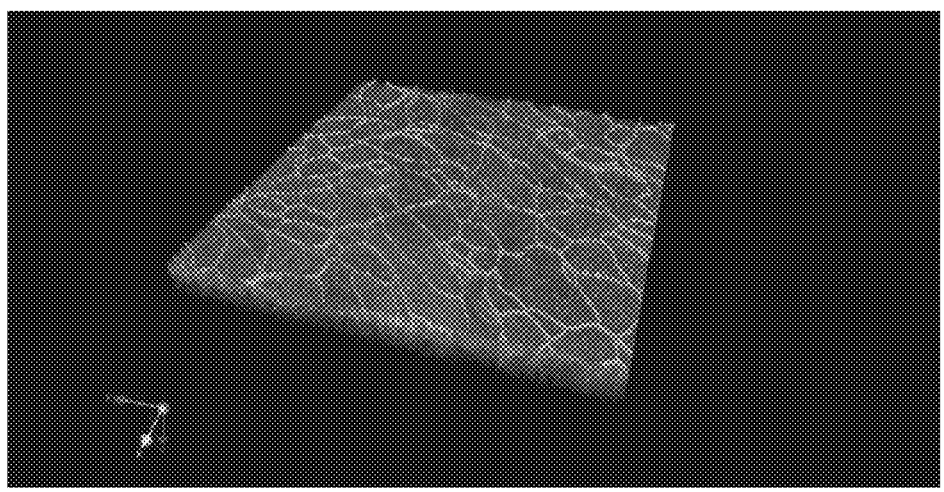

Similarly to Example 1, a cell nucleus labeled image and a ZO-1 labeled image of the fluorescent labeled laminated structure for corneal transplantation were captured, and the obtained planar image data was superimposed to construct a three-dimensional tomographic image. The cell nucleus labeled image of the constructed three-dimensional tomographic image is shown in FIGS. 9A to 9C. FIG. 9A shows a superimposition image of a cell nucleus labeled image and a ZO-1 labeled image, FIG. 9B shows a cell nucleus labeled image, and FIG. 9C shows a ZO-1 labeled image. As a result, a large number of cells having a comparatively small cell nucleus were located on the lower side of the three-dimensional tomographic image, and cells having a comparatively large cell nucleus were located on the upper side at a lower density than the lower side. Similarly to Example 1, the lower cell region and the upper cell region were divided from the three-dimensional tomographic image, and one planar stacked image was produced for each cell region.

Figure 10:
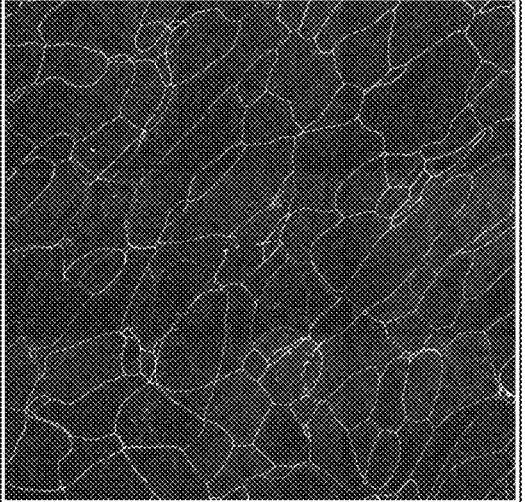
FIG. 10 shows ZO-1 labeled images (left) of an upper planar stacked image and a lower planar stacked image and an image (right) after string detection in Example 3.
Figure 11:
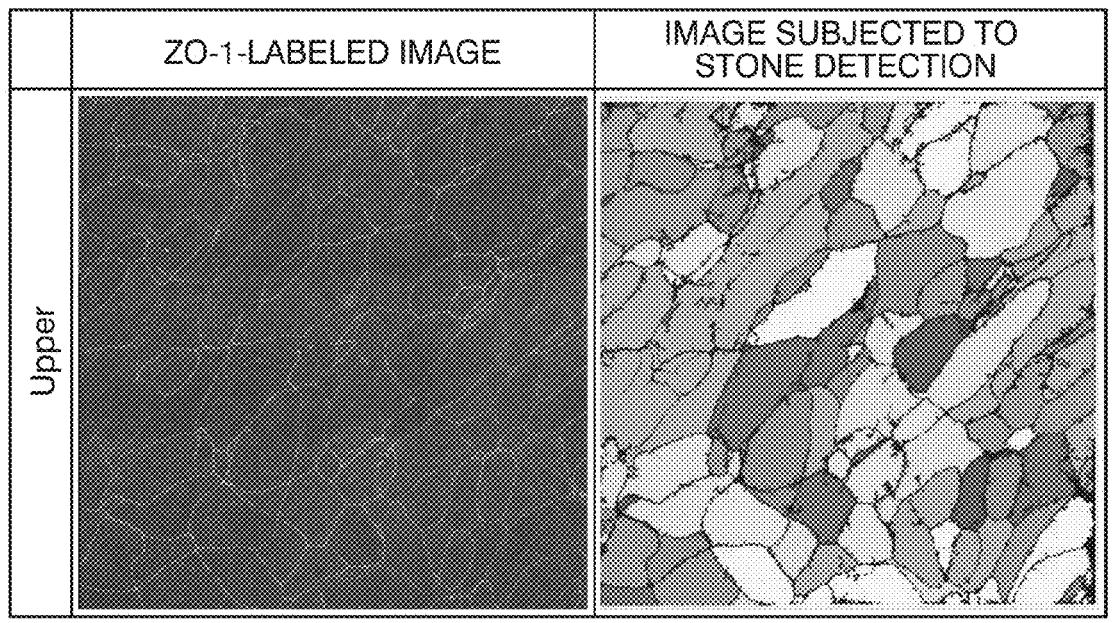
FIG. 11 shows a ZO-1 labeled image (left) of an upper planar stacked image and an image (right) after stone detection in Example 3.

As a result, while a shape of a network structure was observed in the ZO-1 labeled image of the upper planar stacked image, there were no fluorescently labeled images in the lower planar stacked image. Each ZO-1 labeled image was subjected to string detection (a method of detecting a filamentous network structure) or stone detection (a method of detecting one network structure as a stone pavement) was performed. FIG. 10 shows a ZO-1 labeled image (left) and an image (right) after string detection of an upper planar stacked image and a lower planar stacked image. FIG. 11 shows a ZO-1 labeled image (left) and an image (right) after stone detection of an upper planar stacked image. As a result, while 122 stones were detected from the ZO-1 labeled image of the upper planar stacked image, in the lower planar stacked image, the entire image was detected as one stone.

Figure 12:
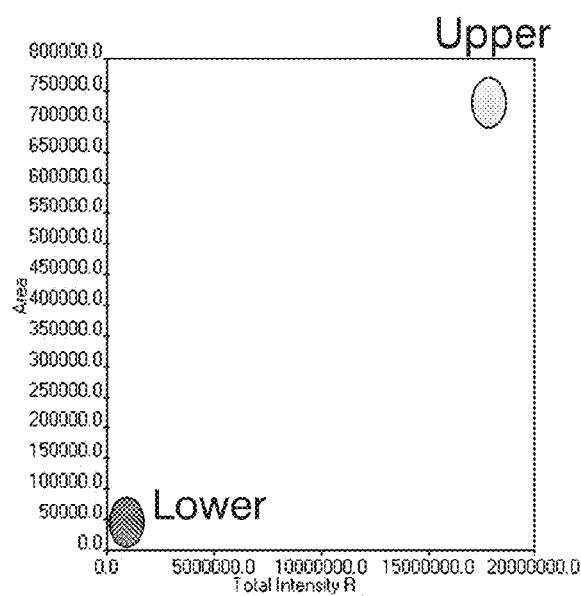
FIG. 12 is a diagram showing an upper planar stacked image and a lower planar stacked image in Example 3 when the horizontal axis represents a total luminance value per image of a ZO-1 labeled image and the vertical axis represents the total area of pixels having a luminance value per pixel equal to or greater than a threshold value.

For the obtained upper planar stacked image and lower planar stacked image, the total luminance value per image in the ZO-1 labeled image and the total area of pixels having a luminance value per pixel equal to or greater than a threshold value were measured. In FIG. 12, the horizontal axis represents the total luminance value per image of each planar stacked image, and the vertical axis represents the total area of the pixels having a luminance value per pixel equal to or greater than the threshold value. For the obtained upper planar stacked image and lower planar stacked image, the average luminance value per pixel in the ZO-1 labeled image and the total area of the pixels having a luminance value per pixel equal to or greater than the threshold value were measured. The measurement results are shown in Table 3. As a result, the average luminance value per pixel in the fluorescent labeled image of ZO-1 of the upper planar stacked image, the sum of the luminance values of all pixels, and the total area of the pixels having a luminance value per pixel equal to or greater than the threshold value were greater than the fluorescent labeled image of ZO-1 of the lower planar stacked image. From these results, it was evaluated that the laminated structure for corneal transplantation was normal and suitable for corneal transplantation.

|  | Average luminance value per pixel | Total area of pixels having luminance value per pixel equal to or greater than threshold value |
| --- | --- | --- |
| Upper | 243000 | 14000 |
| Lower | 18600 | 2500 |

Example 4

The cell nucleus and panCK of the laminated structure for corneal transplantation were fluorescently labeled, and evaluation was performed by the evaluation method of the invention.

First, the cell nucleus and panCK of the laminated structure for corneal transplantation were fluorescently labeled. In fluorescent labeling of panCK, an unlabeled anti-panCK antibody (manufactured by Progen, Product Number: 61006), or an anti-panCK antibody (biotin labeled anti-panCK antibody) directly labeled with biotin in advance was used. The labeling of biotin to the anti-panCK antibody was performed using Biotin Labeling kit-SH (manufactured by Dojindo).

Specifically, the cell nucleus and panCK of the laminated structure for corneal transplantation were fluorescently labeled in the same manner as in Example 3, except that an unlabeled anti-panCK antibody and a biotin labeled anti-panCK antibody were used, instead of an unlabeled anti-ZO-1 antibody and a biotin labeled anti-ZO-1 antibody.

Figure 13A:
FIGS. 13A to 13C show a three-dimensional tomographic image constructed in Example 4.
Figure 13B:
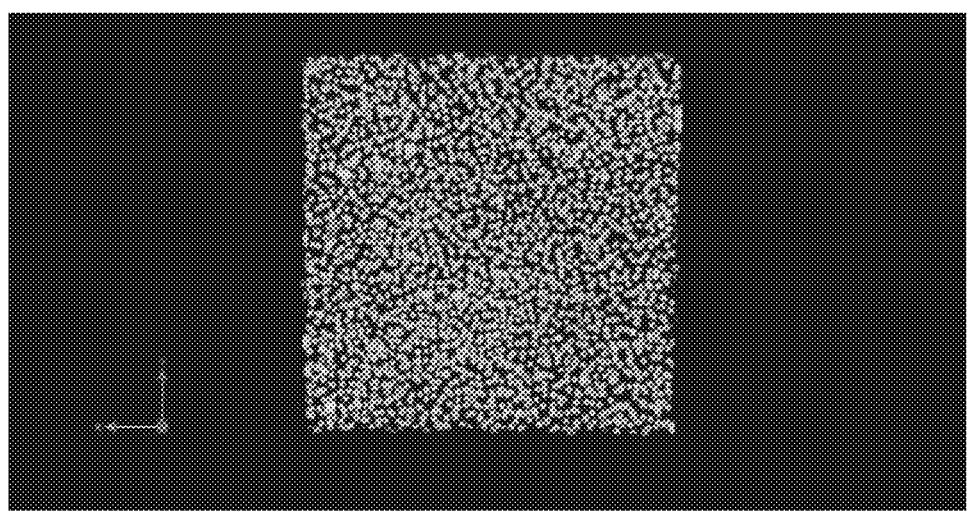
Figure 13C:
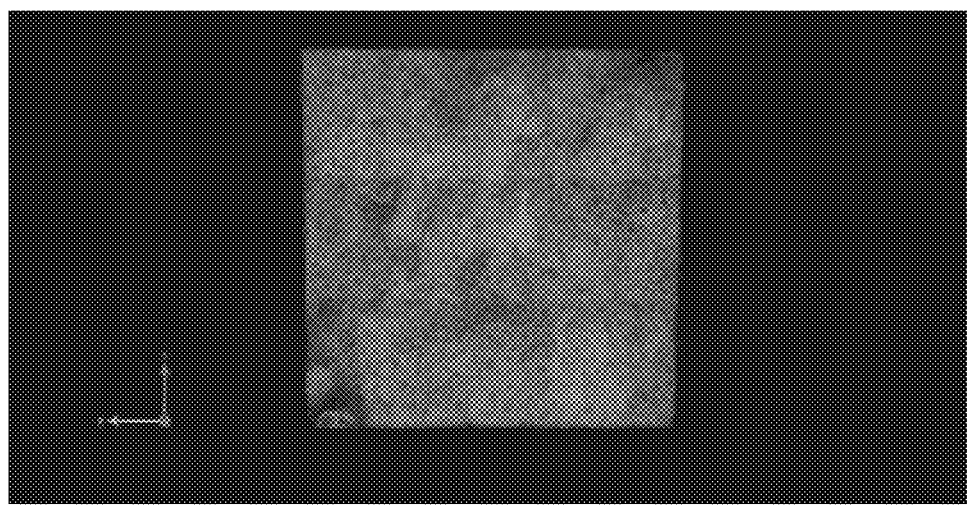
Figure 14:
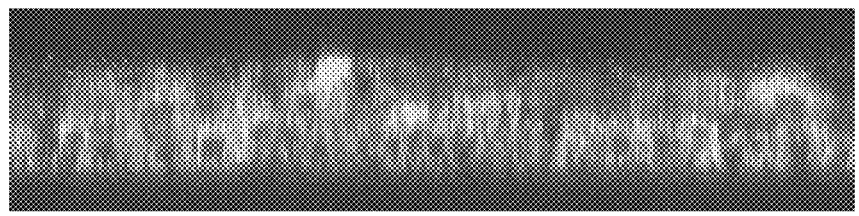
FIG. 14 is a sectional view of a panCK labeled image perpendicular to the bottom of a three-dimensional tomographic image in Example 4.

Similarly to Example 1, a cell nucleus labeled image and a panCK labeled image of the fluorescent labeled laminated structure for corneal transplantation were captured, and the obtained planar image data was superimposed to construct a three-dimensional tomographic image. The cell nucleus labeled image of the constructed three-dimensional tomographic image is shown in FIGS. 13A to 13C. FIG. 13A shows a superimposition image of a cell nucleus labeled image and a panCK labeled image, FIG. 13B shows a cell nucleus labeled image, and FIG. 13C shows a panCK labeled image. FIG. 14 is a sectional view of a panCK labeled image perpendicular to the bottom of a three-dimensional tomographic image. As a result, a large number of cells having a comparatively small cell nucleus were located on the lower side of the three-dimensional tomographic image, and cells having a comparatively large cell nucleus were located on the upper side at a lower density than the lower side. panCK was substantially fluorescently labeled so as to be the same on both the upper side and the lower side of the three-dimensional tomographic image. Similarly to Example 1, the lower cell region and the upper cell region were divided from the three-dimensional tomographic image, and one planar stacked image was produced for each cell region.

Figure 15A:
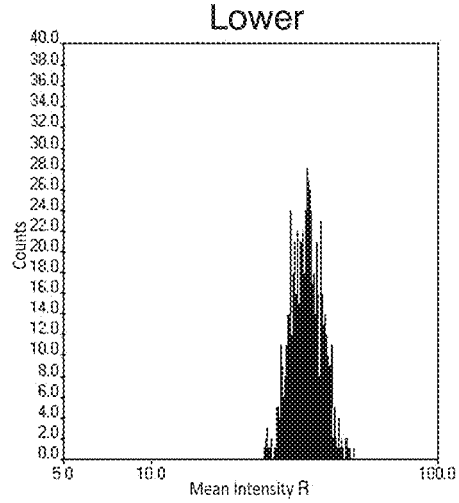
FIGS. 15A to 15C are diagrams relating to Example 4 when the horizontal axis represents an average luminance value per pixel in a cytoplasmic region of a panCK labeled image of each planar stacked image and the vertical axis represents the number (Counts) of cells.
Figure 15B:
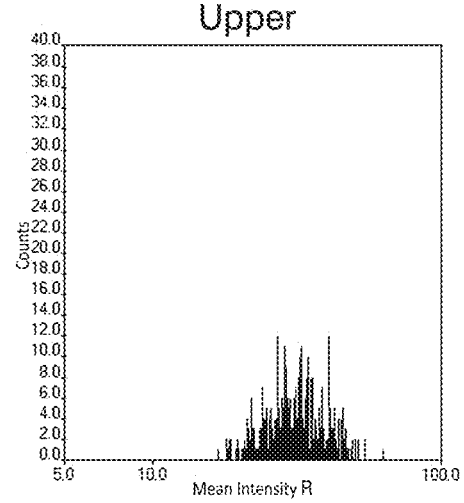
Figure 15C:
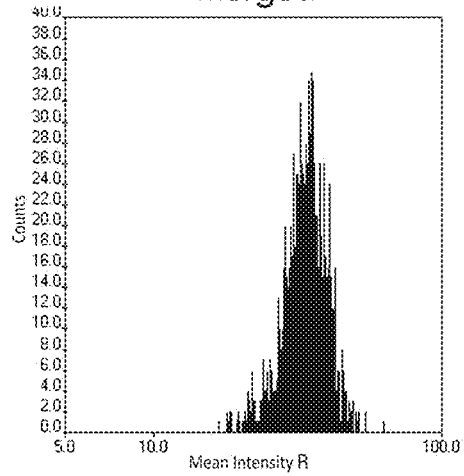

A cytoplasmic region was determined from the cell nucleus image of each obtained planar stacked image, and the average luminance value per pixel in the cytoplasmic region of the panCK labeled image was measured. The measurement result is shown in FIGS. 15A to 15C. FIG. 15A shows the result of the lower planar stacked image, FIG. 15B shows the result of the upper planar stacked image, and FIG. 15C is a diagram when the results of the lower planar stacked image and the upper planar stacked image are superimposed. As a result, the average luminance value per pixel in each cytoplasmic region of the labeled image of panCK of the upper planar stacked image was substantially the same as the fluorescent labeled image of panCK of the lower planar stacked image. Therefore, it was evaluated that the laminated structure for corneal transplantation was normal and suitable for corneal transplantation.

Example 5

Figure 16B:
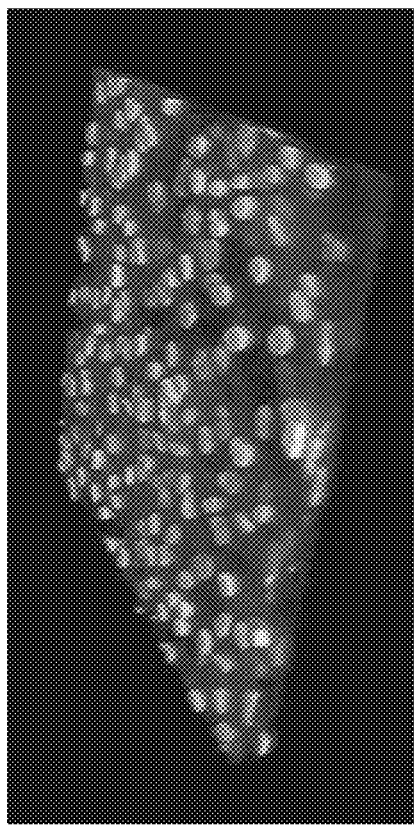
FIGS. 16A to 16D are sectional views of a three-dimensional tomographic image of a panCK labeled image perpendicular to the bottom of the three-dimensional tomographic image in Example 5.
Figure 16D:
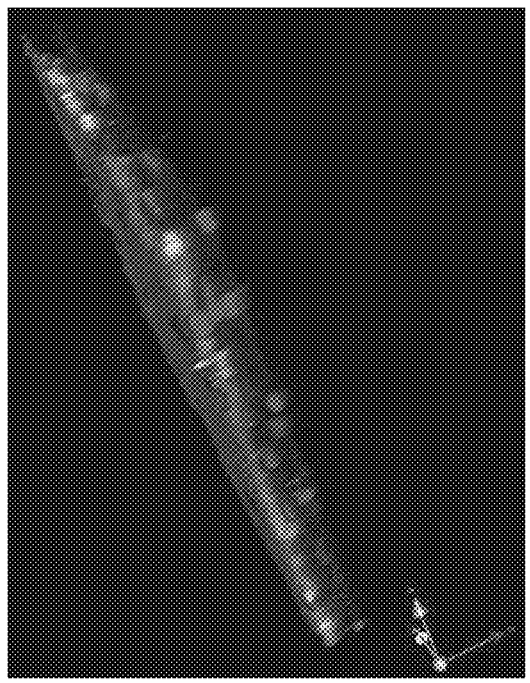
Figure 16A:
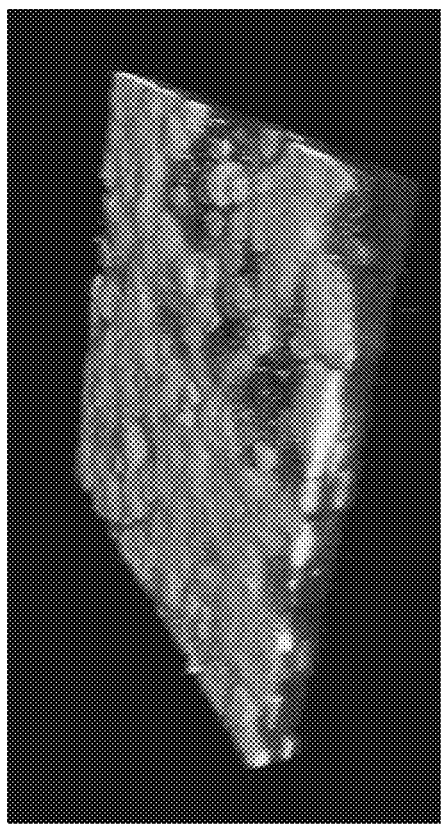
Figure 16C:
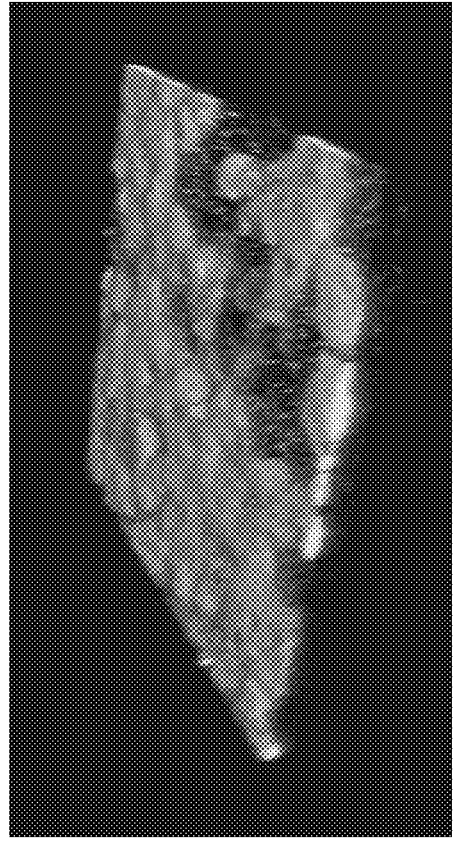

For a laminated structure for corneal transplantation produced by the same method as the laminated structure for corneal transplantation used in Example 4, the cell nucleus and panCK were fluorescently labeled in the same manner as Example 4, except that the culturing of epithelial stem cells was performed using 10% FBS-contained D'MEM medium, a cell nucleus labeled image and a panCK labeled image of the fluorescent labeled laminated structure for corneal transplantation were captured, and the obtained planar image data was superimposed to construct a three-dimensional tomographic image. FIGS. 16A to 16D are sectional views showing the constructed three-dimensional tomographic image perpendicular to the bottom of the three-dimensional tomographic image. FIG. 16A shows a superimposition image of a cell nucleus labeled image and a panCK labeled image, FIG. 16B shows a cell nucleus labeled image, and FIG. 16C shows a panCK labeled image. FIG. 16D is a sectional view perpendicular to the bottom of a superimposition image of a cell nucleus labeled image and a panCK labeled image. As a result, panCK was expressed only on the upper side of the three-dimensional tomographic image.

Figure 17A:
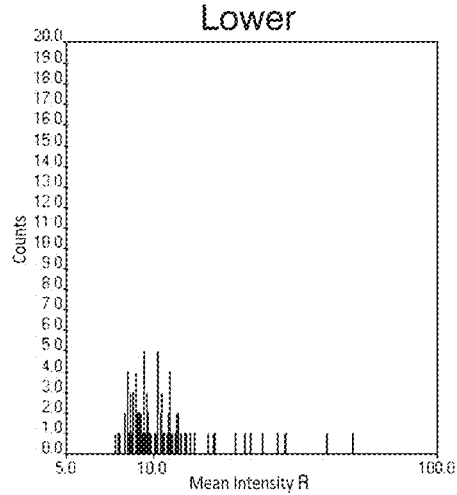
FIGS. 17A to 17C are diagrams relating to Example 5 when the horizontal axis represents an average luminance value per pixel in a cytoplasmic region of a panCK labeled image of each planar stacked image and the vertical axis represents the number (Counts) of cells.
Figure 17B:
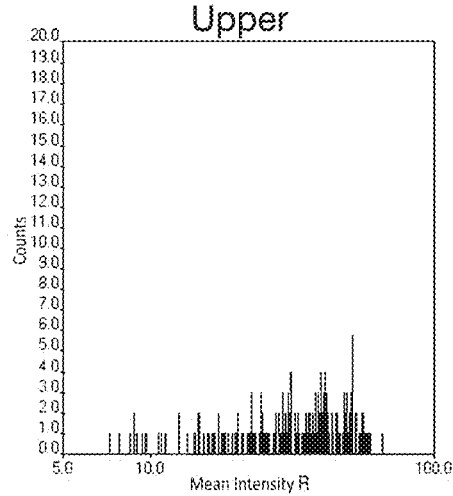
Figure 17C:
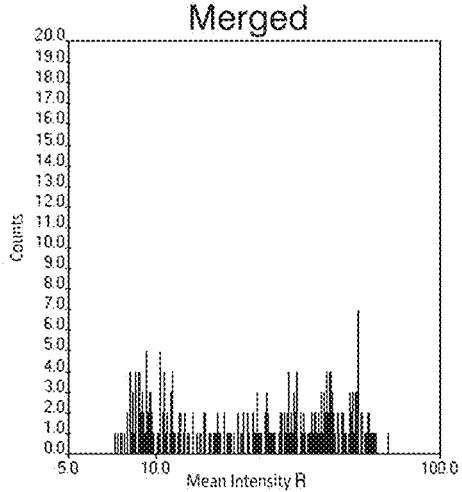

A cytoplasmic region was determined from the cell nucleus image of each obtained planar stacked image, and the average luminance value per pixel in the cytoplasmic region of the panCK labeled image was measured. The measurement result is shown in FIGS. 17A to 17C. FIG. 17A shows the result of the lower planar stacked image, FIG. 17B shows the result of the upper planar stacked image, and FIG. 17C is a diagram when the results of the lower planar stacked image and the upper planar stacked image are superimposed. As a result, in the lower planar stacked image, about 85% of all cells were located in a region surrounded by four corners in FIG. 17A, and in the upper planar stacked image, about 93% of all cells were located in a region surrounded by four corners in FIG. 17B. That is, the average luminance value per pixel in each cytoplasmic region of the labeled image of panCK of the upper planar stacked image was clearly greater than the fluorescent labeled image of panCK of the lower planar stacked image.

For the obtained upper planar stacked image and lower planar stacked image, the total luminance value per image in the panCK labeled image, the average luminance value per pixel, the total area of pixels having a luminance value per pixel equal to or greater than a threshold value, and the ratio (%) of the pixels having a luminance value per pixel equal to or greater than the threshold value per image were measured. The measurement results are shown in Table 4. From the results, it was confirmed that the average luminance value per pixel in each cytoplasmic region of the labeled image of panCK of the upper planar stacked image was greater than the fluorescent labeled image of panCK of the lower planar stacked image. From these results, it was evaluated that the laminated structure for corneal transplantation was not normal and suitable for corneal transplantation.

|  | Total luminance value per image | Average luminance value per pixel | Total area of pixels having luminance value per pixel equal to or greater than threshold value | Ratio (%) of pixels having luminance value per pixel equal to or greater than threshold value per image |
|---|---|---|---|---|
| Upper | 477200000 | 590.3 | 808400 | 85.1 |
| Lower | 584600000 | 668.1 | 874900 | 92.1 |

The average value (the average value of brightness per cell) of the total luminance value per cell in the panCK labeled image and the ratio (%) of cells (positive cells) including pixels having a luminance value per pixel equal to or greater than a threshold value to the total number of cells in each image were measured, and the measurement results are shown in Table 5. It was confirmed that panCK was expressed to be the same on both the upper planar stacked image and the lower planar stacked image, and almost all cells expressed panCK.

|  | Average brightness of each cell | Ratio (%) of positive cells to the total number of cells in each image |
|---|---|---|
| Upper | 543 | 98.6 |
| Lower | 649 | 99.8 |

Example 6

The cell nucleus and p63 of the laminated structure for corneal transplantation were fluorescently labeled, and evaluation was performed by the evaluation method of the invention.

First, a cell nucleus and p63 of a laminated structure for corneal transplantation were fluorescently labeled. In fluorescent labeling of p63, an unlabeled anti-p63 antibody (manufactured by LIFESPAN, Product Number: LS-C118547) or the same unlabeled anti-p63 antibody (manufactured by Santacruz, Product Number: sc-8431) was used.

Specifically, a cell nucleus and p63 of a laminated structure for corneal transplantation were fluorescently labeled in the same manner as in Example 1, except that an unlabeled anti-p63 antibody and an Alexa555 goat anti-rabbit IgG (H+L) antibody were used instead of instead of an unlabeled anti-AE5 antibody and an Aleaxa488 goat anti-mouse IgG (H+L) antibody.

As in Example 1, a cell nucleus labeled image and a p63 labeled image of a fluorescently labeled laminated structure for corneal transplantation were captured, and obtained planar image data was superimposed to construct a three-dimensional tomographic image.

Figure 18A:
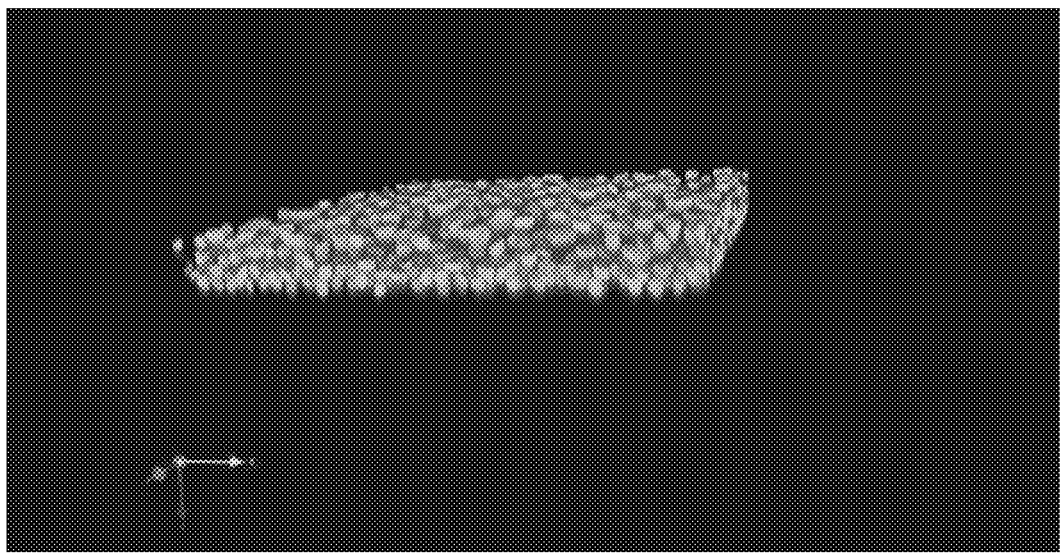
FIGS. 18A and 18B show a three-dimensional tomographic image constructed in Example 6.
Figure 18B:
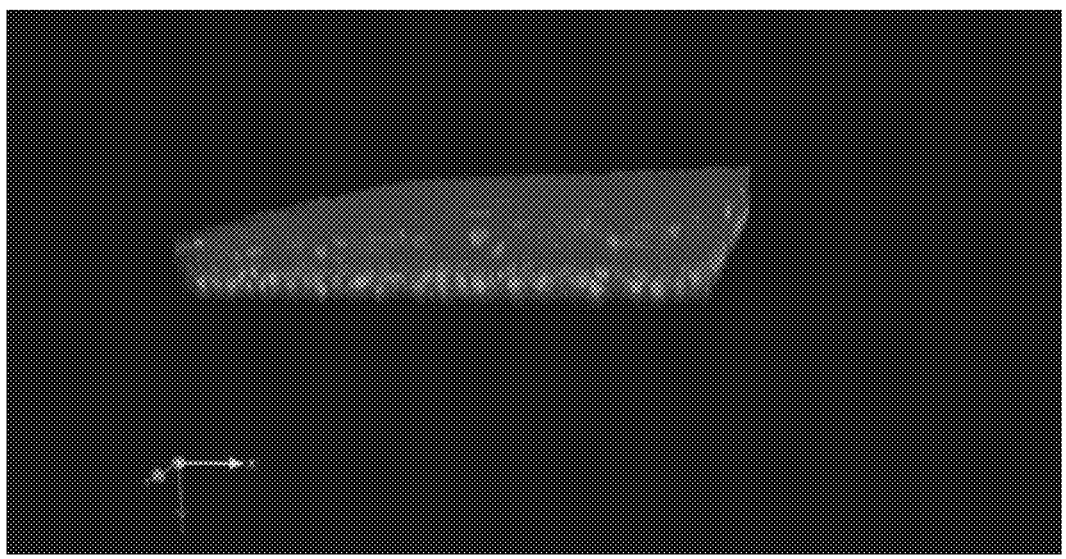
Figure 19:
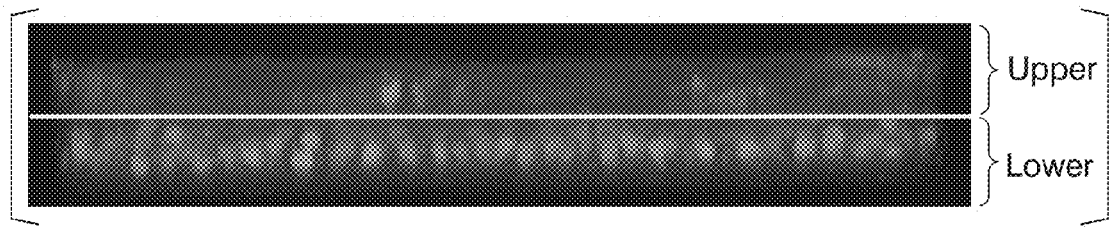
FIG. 19 is a sectional view of a p63 labeled image perpendicular to the bottom of a three-dimensional tomographic image in Example 6.

A cell nucleus labeled image of the constructed three-dimensional tomographic image is shown in FIGS. 18A and 18B. FIG. 18A shows a cell nucleus labeled image, and FIG. 18B shows a p63 labeled image. FIG. 19 is a sectional view showing a p63 labeled image perpendicular to the bottom of a three-dimensional tomographic image. As a result, a large number of cells having a comparatively small cell nucleus were located on the lower side of the three-dimensional tomographic image, and cells having a comparatively large cell nucleus were located on the upper side at a lower density than the lower side. It was confirmed that a large amount of p63 was expressed on the lower side of the three-dimensional tomographic image. Similarly to Example 1, the lower cell region and the upper cell region were divided from the three-dimensional tomographic image, and one planar stacked image was produced for each cell region.

Figure 20:
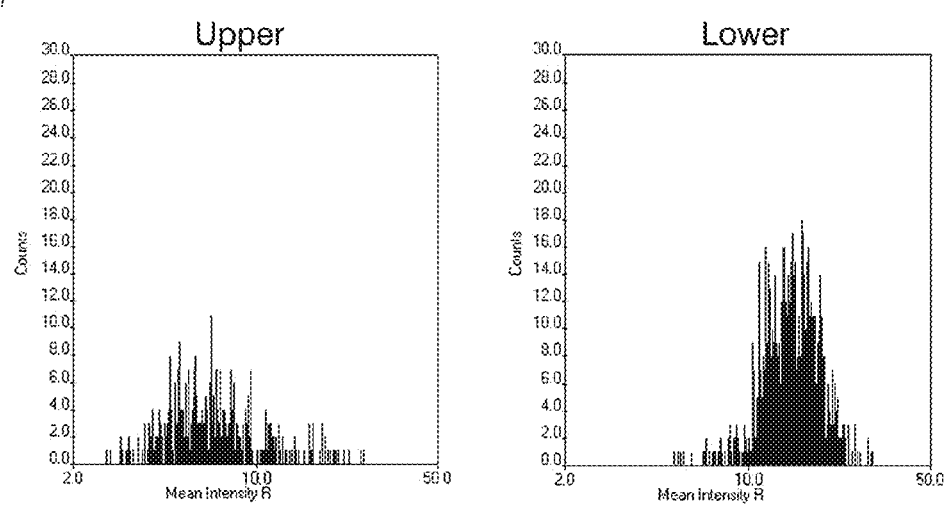
FIG. 20 is a diagram relating to Example 6 when the horizontal axis represents an average luminance value per pixel of p63 labeled images of an upper planar stacked image and a lower planar stacked image and the vertical axis represents the number (Counts) of cells.
Figure 21:
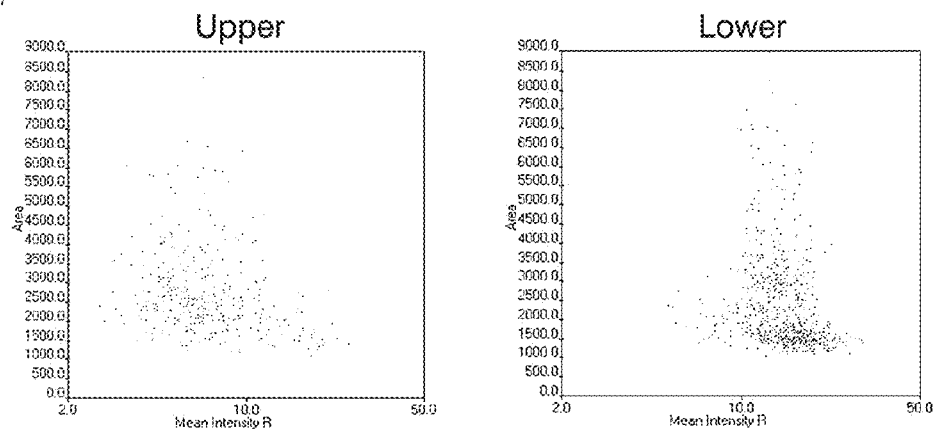
FIG. 21 is a diagram showing an upper planar stacked image and a lower planar stacked image in Example 6 when the horizontal axis represents an average luminance value per cell nucleus of a p63 labeled image and the vertical axis represents the total area of pixels having a luminance value per pixel in one cell nucleus equal to or greater than a threshold value.

For the obtained upper planar stacked image and lower planar stacked image, the average luminance value per pixel of the p63 labeled image and the total area of pixels having a luminance value per pixel equal to or greater than a threshold value were measured. In FIG. 20, the horizontal axis represents the average luminance value per pixel of the p63 labeled image of each planar stacked image, and the vertical axis represents the number (Counts) of cells. In FIG. 21, for each planar stacked image, the horizontal axis represents the average luminance value per cell nucleus of the p63 labeled image, and the vertical axis represents the total area of pixels having a luminance value per pixel in each cell nucleus equal to or greater than the threshold value.

In FIGS. 20 and 21, "Upper" represents the result of the upper planar stacked image, and "Lower" represents the result of the lower planar stacked image. As a result, in a region surrounded by four corners of FIG. 20, about 83% of all cells were located in the upper planar stacked image, and about 94% of all cells were located in the lower planar stacked image. That is, the average luminance value per pixel in each cell nucleus region of the labeled image of p63 was greater in the lower planar stacked image than in the upper planar stacked image.

For the obtained upper planar stacked image and lower planar stacked image, the average value (the average value of brightness per cell) of the total luminance value per cell (per cell nucleus) in the p63 labeled image, and the ratio (%) of cells (positive cells) including pixels having a luminance value per pixel equal to or greater than the threshold value to the total number of cells (the total number of cells in Upper+Lower) in the upper planar stacked image and the lower planar stacked image were measured. The measurement results are shown in Table 6. It was confirmed that, while a few p63 positive cells were also located in the upper planar stacked image, most of cells in the lower planar stacked image were p63 positive cells. The average value of brightness per cell was clearly greater in the lower planar stacked image than in the upper planar stacked image. From these results, it was evaluated that the laminated structure for corneal transplantation was normal and suitable for corneal transplantation.

|  | Average brightness of each cell | Ratio (%) of positive cells to the total number of cells in Upper + Lower |
| --- | --- | --- |
| Upper | 552 | 6.4 |
| Lower | 1666 | 80.5 |

Example 7

Figure 22:
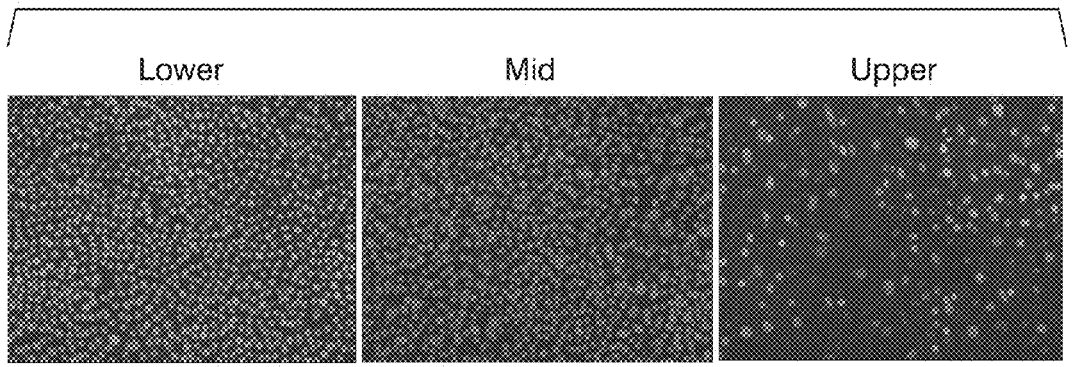
FIG. 22 shows a cell nucleus labeled image of each planar stacked image in Example 7.

The three-dimensional tomographic image constructed in Example 6 was divided visually into three cell regions of a lower cell region where a comparatively small cell group was located, a middle cell region where a comparatively larger cell group than the lower cell region was located, and an upper cell region where a flat and large cell group was located, and one planar stacked image was produced for each cell region in the same manner as in Example 1. FIG. 22 shows a cell nucleus labeled image of an obtained planar stacked image. In FIG. 22, "Lower" represents a planar stacked image produced from the lower cell region, "Mid" represents a planar stacked image produced from the middle cell region, and "Upper" represents a planar stacked image produced from the upper cell region.

Figure 23:
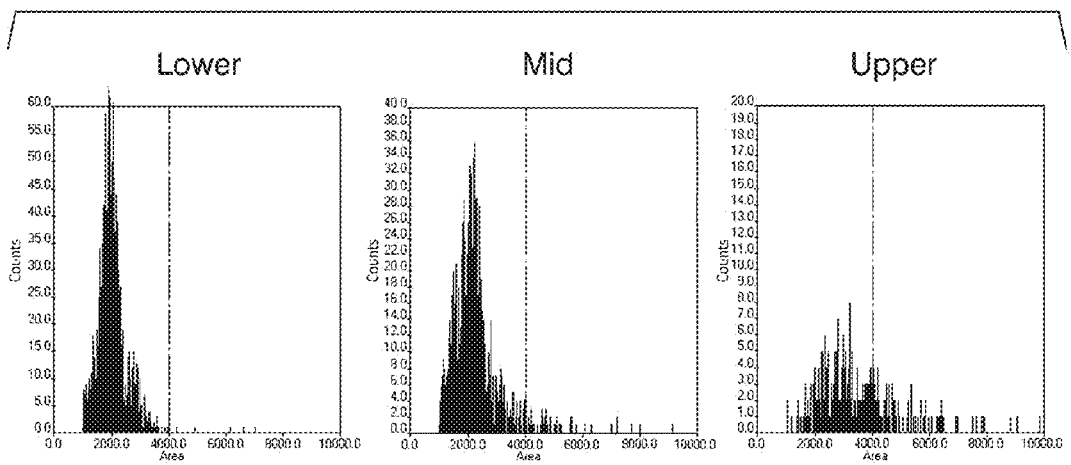
FIG. 23 is a diagram relating to Example 7 when the horizontal axis represents the total area of pixels (the area of a cell nucleus) having a luminance value per pixel in a cell nucleus image of each planar stacked image equal to or greater than a threshold value and the vertical axis represents the number (Counts) of cells.

The total area (that is, the area of the cell nucleus) of pixels having a luminance value per pixel in the cell nucleus image of each planar stacked image equal to or greater than the threshold value was measured. The measurement result is shown in FIGS. 23A to 23C. Left graph of FIG. 23 shows the result of a planar stacked image produced from the lower cell region. Middle graph of FIG. 23 shows the result of a planar stacked image produced from the middle cell region. Right graph of FIG. 23 shows the result of a planar stacked image produced from the upper cell region. The number of cells in the cell nucleus image of each planar stacked image, the average area value of the cell nucleus, and the ratio of cells having a cell nucleus equal to or greater than 4000 pixels are shown in Table 7. In Table 7, "Lower", "Mid", and "Upper" are the same as in FIG. 22. As a result, it was confirmed that the number of cells in the lower cell region was largest and becomes smaller on the upper side of the three-dimensional tomographic image. To the contrary, the area of the cell nucleus becomes larger on the upper side of the three-dimensional tomographic image. Therefore, it was evaluated that the laminated structure for corneal transplantation was normal and suitable for corneal transplantation.

|  | Number of cell nuclei | Average area value (pixel) of cell nuclei | Ratio (%) of cells having cell nucleus area equal to or greater than 4000 pixels |
| --- | --- | --- | --- |
| Upper | 287 | 3530 | 30 |
| Mid | 990 | 2310 | 5.2 |
| Lower | 1306 | 2029 | 0.4 |

The image analysis method and the evaluation method of the invention can be suitably used for analysis or evaluation of a laminated structure for transplantation with cell populations forming a layered structure, and can be thus used in the field of regenerative medicine.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A method of analyzing an image of a cell in a laminated structure having at least one cell layer, the method comprising:
    (a) fluorescently labeling a cell nucleus and one or more other types of biomolecules in the laminated structure having the at least one cell layer;
    (b) acquiring a plurality of planar tomographic fluorescent labeled images in different height directions from the laminated structure for each type of fluorescently labeled biomolecules after the (a) labeling;
    (c) superimposing a planar tomographic fluorescent labeled image group acquired in the (b) acquiring to construct a three-dimensional tomographic image;
    (d) dividing the constructed three-dimensional tomographic image into one or two or more cell regions;
    (e) producing one planar stacked image for each divided cell region after the (d) dividing; and
    (f) performing image analysis on each produced planar stacked image to analyze cells in the laminated structure,
    wherein the cell regions divided in the (d) dividing are regions which include one or two or more cell layers in the three-dimensional tomographic image and are parallel to a bottom of the three-dimensional tomographic image.

2. The method according to claim 1,
    wherein, in the (d) dividing, a cell region of one cell layer including a specific type of cells from among the determined cell regions is determined by:
    (i) specifying, as a cell-free cross section, a cross section, in which there are no cell nuclei of the specific type of cells and which has a smallest height from a bottom of the laminated structure, from among cross sections parallel to the bottom of the three-dimensional tomographic image;
    (ii) specifying, as a cell bottom reference cross section, a cross section, which is located above the cell-free cross section, has the total luminance value of cells to be analyzed per image of the cell nucleus labeled image 10 to 50% greater than the cell-free cross section, and is closest to the cell-free cross section, from among the cross sections parallel to the bottom of the three-dimensional tomographic image; and (iii) determining, as the cell region of the cell layer including the specific type of cells, a region from a cross section located 5 to 10 μm below the cell bottom reference cross section in the height direction of the laminated structure to a cross section located 15 to 25 μm above in the height direction of the laminated structure.

3. The method according to claim 2,
wherein the specific type of cells are stem cells.

4. The method according to claim 1, wherein the laminated structure has a first cell layer including a first type of cells, and a second cell layer including a second type of cells different from the first type above the first cell layer.

5. The method according to claim 4,
wherein, in the (a) labeling, in addition to the cell nucleus, one or more types of biomolecules selected from a group including biomolecules more expressed in the first type of cells than the second type of cells and biomolecules more expressed in the second type of cells than the first type of cells are fluorescently labeled.

6. The method according to claim 4,
wherein the first type of cells are stem cells, and
the second type of cells are cells which are differentiated from the stem cells.

7. The method according to claim 4,
wherein, in the (d) dividing, a cell region of the first cell layer and a cell region of the second cell layer are divided.

8. The method according to claim 1,
wherein the laminated structure is formed by culturing corneal epithelial stem cells or oral mucosal stem cells.

9. The method according to claim 1,
wherein, during the image analysis in (f), one or more selected from a group including an average luminance value per pixel of each planar stacked image, a sum of luminance values of all pixels, a total area of pixels having a luminance value per pixel equal to or greater than a threshold value, and a shape of a region of pixels having a luminance value per pixel equal to or greater than the threshold value are analyzed.

10. A method of evaluating a laminated structure for corneal transplantation which is formed by culturing epithelial stem cells and used for corneal transplantation, the method comprising:

(a') fluorescently labeling a cell nucleus and one or more types of biomolecules selected from a group including biomolecules specific to epithelial stem cells, biomolecules specific to epithelial cells after differentiation or a surrounding tissue, and biomolecules in both the epithelial stem cells and the epithelial cell after differentiation, in the laminated structure;

(b') acquiring a plurality of planar tomographic fluorescent labeled images in different height directions from the laminated structure for each type of fluorescently labeled biomolecules after the (a') labeling;

(c') superimposing a planar tomographic fluorescent labeled image group acquired in the (b') acquiring to construct a three-dimensional tomographic image;

(d') dividing the constructed three-dimensional tomographic image into a lower cell region of a cell layer including epithelial stem cells and an upper cell region above and adjacent to the lower cell region;

(e') producing one planar stacked image for each divided region after the (d') dividing; and (f') performing image analysis on each produced planar stacked image and evaluating the laminated structure based on a result of the analysis, wherein the cell regions divided in the (d') dividing are regions which include one or two or more cell layers in the three-dimensional tomographic image and are parallel to a bottom of the three-dimensional tomographic image.

11. The method according to claim 10,
wherein, in the (d') dividing, the lower cell region is determined by:

(i') specifying, as a cell-free cross section, a cross section, in which there are no cell nuclei and which has a smallest height from a bottom of the laminated structure, from among cross sections parallel to the bottom of the three-dimensional tomographic image;

(ii') specifying, as a stem cell bottom reference cross section, a cross section which is located above the cell-free cross section, has a total luminance value per image of the cell nucleus labeled image 10 to 50% greater than the cell-free cross section, and is closest to the cell-free cross section, from among the cross sections parallel to the bottom of the three-dimensional tomographic image; and (iii') determining, as the lower cell region, a region from a cross section 5 to 10 μm below the stem cell bottom reference cross section in the height direction of the laminated structure to a cross section 15 to 25 μm above in the height direction of the laminated structure.

12. The method according to claim 10,
wherein, in the (d') dividing, the upper cell region and the lower cell region are determined by:

(i"-1) specifying, as a lower cell-free cross section, a cross section, in which there are no cell nuclei and which has a smallest height from a bottom of the laminated structure, from among cross sections parallel to the bottom of the three-dimensional tomographic image;

(i"-2) specifying, as an upper cell-free cross section, a cross section, in which there are no cell nuclei and which has a greatest height from the bottom of the laminated structure, from among the cross sections parallel to the bottom of the three-dimensional tomographic image; and (iii") defining a cross section at a same distance from both the lower cell-free cross section and the upper cell-free cross section as an interface, determining a region from the lower cell-free cross section to the interface as the lower cell region, and determining a region from the interface to the upper cell-free cross section as the upper cell region.

13. The method according to claim 10,
wherein, in the (a') labeling, the cell nucleus and one or more types of biomolecules selected from a group including cytokeratin, mucin, and biomolecules constituting the tight junction of epithelial cells, and p63 are fluorescently labeled.

14. The method according to claim 10,
wherein, in the (a') labeling, the cell nucleus and one or more types of biomolecules selected from a group including AE5, MUC16, ZO-1, panCK, and p63 are fluorescently labeled.

15. The method according to claim 10,
wherein: in the (a') labeling, at least the cell nucleus and AE5 are fluorescently labeled, and
in the (f') performing of the image analysis, when an average luminance value per pixel, a sum of luminance values of all pixels, and a total area of pixels having a luminance value per pixel equal to or greater than a threshold value, in a fluorescent labeled image of AE5 of a planar stacked image produced from the upper cell region, are greater than those in a fluorescent labeled image of AE5 of a planar stacked image produced from the lower cell region, it is evaluated that the laminated structure is appropriate for corneal transplantation.

16. The method according to claim 10,
wherein, in the (a') labeling, at least the cell nucleus and MUC16 are fluorescently labeled, and
in the (f') performing of the image analysis, when an average luminance value per pixel, a sum of luminance values of all pixels, and a total area of pixels having a luminance value per pixel equal to or greater than a threshold value, in a fluorescent labeled image of MUC16 of a planar stacked image produced from the upper cell region, are greater than those in a fluorescent labeled image of MUC16 of a planar stacked image produced from the lower cell region, it is evaluated that the laminated structure is appropriate for corneal transplantation.

17. The method according to claim 10,
wherein, in the (a') labeling, at least the cell nucleus and ZO-1 are fluorescently labeled, and
in the (f') performing of the image analysis, when an average luminance value per pixel, a sum of luminance values of all pixels, and a total area of pixels having a luminance value per pixel equal to or greater than a threshold value, in a fluorescent labeled image of ZO-1 of a planar stacked image produced from the upper cell region, are greater than those in a fluorescent labeled image of ZO-1 of a planar stacked image produced from the lower cell region, and a region of pixels having the luminance value per pixel equal to or greater than the threshold value in the fluorescent labeled image of ZO-1 of the planar stacked image produced from the upper cell region has a shape of a network structure, it is evaluated that the laminated structure is appropriate for corneal transplantation.

18. The method according to claim 10, wherein:
in the (a') labeling, at least the cell nucleus and p63 are fluorescently labeled,
in the (f') performing of the image analysis, for each produced planar stacked image, a cell nucleus region is determined based on a labeled image of the cell nucleus, and
when an average luminance value per pixel in each cell nucleus region in a labeled image of p63 of a planar stacked image produced from the upper cell region is greater than that in a fluorescent labeled image of p63 of a planar stacked image produced from the lower cell region, it is evaluated that the laminated structure is appropriate for corneal transplantation.

19. The method according to claim 10, wherein:
in the (f') performing of the image analysis, for each produced planar stacked image, a cell nucleus region is determined based on a labeled image of the cell nucleus, and
when a ratio of the cell nucleus region having an area equal to or greater than a threshold value to all cell nucleus regions in a planar stacked image produced from the upper cell region is greater than a planar stacked image produced from the lower cell region, it is evaluated that the laminated structure is appropriate for corneal transplantation.

20. The method according to claim 10, wherein:
in the (f') performing of the image analysis, for each produced planar stacked image, a cell nucleus region is determined based on a labeled image of the cell nucleus, and
when an average value of areas of the cell nucleus regions in a planar stacked image produced from the upper cell region is three times greater than an average value of areas of the cell nucleus regions in a planar stacked image produced from the lower cell region, it is evaluated that the laminated structure is appropriate for corneal transplantation.

21. The method according to claim 13,
wherein, in the (a') labeling, panCK is further fluorescently labeled,
in the (f') performing of the image analysis, for each produced planar stacked image, a cell nucleus region is determined based on a labeled image of the cell nucleus,
a region which is doughnut-shaped with an outer circumferential portion of each cell nucleus region as an inner circumference and in which a width of the doughnut shape has a regular interval is determined as a cytoplasmic region, and
when an average luminance value per pixel in each cytoplasmic region of a labeled image of panCK of a planar stacked image produced from the upper cell region is the same as that in a fluorescent labeled image of panCK of a planar stacked image produced from the lower cell region, it is evaluated that the laminated structure is appropriate for corneal transplantation.

* * * * *